(12) United States Patent
Anderson et al.

(10) Patent No.: US 8,517,914 B2
(45) Date of Patent: Aug. 27, 2013

(54) SURGICAL ARTICLES AND METHODS FOR TREATING PELVIC CONDITIONS

(75) Inventors: Kimberly A. Anderson, Minnetonka, MN (US); Karen Pilney Montpetit, Minnetonka, MN (US); Kelly Ann Chapman, Minnetonka, MN (US)

(73) Assignee: AMS Research Corporation, Minnetonka, MN (US)

( * ) Notice: Subject to any disclaimer, the term of this patent is extended or adjusted under 35 U.S.C. 154(b) by 760 days.

(21) Appl. No.: 12/447,073

(22) PCT Filed: Oct. 26, 2007

(86) PCT No.: PCT/US2007/022689
§ 371 (c)(1),
(2), (4) Date: Feb. 12, 2010

(87) PCT Pub. No.: WO2008/057269
PCT Pub. Date: May 15, 2008

(65) Prior Publication Data
US 2010/0174134 A1  Jul. 8, 2010

Related U.S. Application Data

(60) Provisional application No. 60/863,049, filed on Oct. 26, 2006, provisional application No. 60/947,044, filed on Jun. 29, 2007.

(51) Int. Cl.
*A61F 2/00* (2006.01)

(52) U.S. Cl.
USPC .......................................... 600/37

(58) Field of Classification Search
USPC ................ 600/29, 30, 37; 128/885; 606/151
See application file for complete search history.

(56) References Cited

U.S. PATENT DOCUMENTS

| | | | |
|---|---|---|---|
| 4,172,458 A | 10/1979 | Pereyra |
| 5,922,026 A | 7/1999 | Chin |
| 6,306,079 B1 | 10/2001 | Trabucco |
| 6,502,578 B2 | 1/2003 | Raz et al. |
| 6,575,897 B1 | 6/2003 | Ory |
| 6,592,515 B2 | 7/2003 | Thierfelder |
| 7,087,065 B2 | 8/2006 | Ulmsten et al. |
| 7,131,943 B2 | 11/2006 | Kammerer |
| 7,131,944 B2 | 11/2006 | Jacquetin |
| 7,175,591 B2 | 2/2007 | Kaladelfos |

(Continued)

FOREIGN PATENT DOCUMENTS

| | | |
|---|---|---|
| DE | 19544162 | 4/1997 |
| EP | 0248544 A1 | 12/1987 |

(Continued)

OTHER PUBLICATIONS

Amundsen, Cindy L. et al., Anatomical Correction of Vaginal Vault Prolapse by Uterosacral Ligament Fixation in Women Who Also Require a Pubovaginal Sling, The Journal of Urology, vol. 169, pp. 1770-1774, (May 2003).

(Continued)

*Primary Examiner* — Christine Matthews
(74) *Attorney, Agent, or Firm* — Kagan Binder, PLLC

(57) ABSTRACT

Described are pelvic implants and methods of surgically placing pelvic implants, that provide treatment for pelvic floor disorders by support of the levator.

10 Claims, 11 Drawing Sheets

(56) References Cited

U.S. PATENT DOCUMENTS

| | | | |
|---|---|---|---|
| 7,347,812 B2 | 3/2008 | Mellier | |
| 7,351,197 B2 | 4/2008 | Montpetit et al. | |
| 7,393,320 B2 | 7/2008 | Montpetit et al. | |
| 7,407,480 B2 | 8/2008 | Staskin | |
| 7,494,495 B2 | 2/2009 | Delorme et al. | |
| 7,500,945 B2 | 3/2009 | Cox | |
| 7,517,313 B2 | 4/2009 | Thierfelder et al. | |
| 7,588,598 B2 | 9/2009 | Delorme et al. | |
| 7,608,036 B2 | 10/2009 | Raz et al. | |
| 7,740,576 B2 | 6/2010 | Hodroff | |
| 7,794,385 B2 | 9/2010 | Rosenblatt | |
| 7,985,175 B2 * | 7/2011 | Toso et al. | 600/37 |
| 2002/0028980 A1 | 3/2002 | Thierfelder et al. | |
| 2004/0039453 A1 | 2/2004 | Anderson et al. | |
| 2004/0267088 A1 | 12/2004 | Kammerer | |
| 2005/0004427 A1 | 1/2005 | Cervigni | |
| 2005/0199249 A1 | 9/2005 | Karram | |
| 2005/0245787 A1 | 11/2005 | Cox et al. | |
| 2005/0278037 A1 | 12/2005 | Delorme et al. | |
| 2005/0283189 A1 | 12/2005 | Rosenblatt et al. | |
| 2006/0058578 A1 * | 3/2006 | Browning | 600/37 |
| 2006/0122457 A1 | 6/2006 | Kovac | |
| 2006/0173237 A1 | 8/2006 | Jacquetin | |
| 2006/0195011 A1 | 8/2006 | Arnal | |
| 2007/0173864 A1 | 7/2007 | Chu | |
| 2008/0039678 A1 | 2/2008 | Montpetit et al. | |
| 2009/0005634 A1 | 1/2009 | Rane | |
| 2009/0012353 A1 | 1/2009 | Beyer | |
| 2009/0240102 A1 | 9/2009 | Rane et al. | |
| 2010/0152528 A1 | 6/2010 | Chapmenan et al. | |

FOREIGN PATENT DOCUMENTS

| | | |
|---|---|---|
| EP | 1060714 A3 | 9/2002 |
| FR | 285217 | 10/2004 |
| IT | 1299162 | 4/1998 |
| WO | WO9835632 A1 | 8/1998 |
| WO | WO9916381 A1 | 4/1999 |
| WO | WO0064370 A1 | 2/2000 |
| WO | WO0027304 A1 | 5/2000 |
| WO | WO0047812 A1 | 10/2000 |
| WO | WO0106951 A1 | 2/2001 |
| WO | WO02078552 A1 | 10/2002 |
| WO | WO03003778 A1 | 4/2003 |
| WO | WO03028585 A2 | 4/2003 |
| WO | WO03047476 A1 | 6/2003 |
| WO | WO03068107 A1 | 8/2003 |
| WO | WO03073960 A1 | 9/2003 |
| WO | WO03096929 A1 | 11/2003 |
| WO | WO2004012626 A1 | 2/2004 |
| WO | WO2004045457 A1 | 6/2004 |
| WO | WO2005037132 A2 | 4/2005 |
| WO | WO2005087153 A2 | 9/2005 |
| WO | WO2005094741 A1 | 10/2005 |
| WO | WO2005112842 A1 | 12/2005 |
| WO | WO2006108145 A1 | 10/2006 |
| WO | WO2007002071 A1 | 1/2007 |
| WO | WO2007014241 A1 | 2/2007 |
| WO | WO2007016083 A1 | 2/2007 |
| WO | WO2007059199 A2 | 5/2007 |
| WO | WO2007081955 A1 | 7/2007 |
| WO | WO2007146784 A2 | 12/2007 |
| WO | WO2007149348 A2 | 12/2007 |
| WO | WO2008124056 A1 | 10/2008 |
| WO | WO2009017680 A2 | 2/2009 |

OTHER PUBLICATIONS

Burch, John C., Urethrovaginal Fixation to Cooper's Ligament for Correction of Stress Incontinence, Cystocele, and Prolapse, Am. J. Obst. & Gyn. vol. 31, pp. 281-290 (1961).

Cervigni, Mauro et al., The Use of Synthetics in the Treatment of Pelvic Organ Prolapse, Dunction and Female Urology, vol. 11, pp. 429-435 (2001) Voidingysf.

Diana, et al., Treatment of Vaginal Vault Prolapse With Abdominal Sacral Colpopexy Using Prolene Mesh, American Journal of Surgery, vol. 179, pp. 126-128, (Feb. 2000).

Eglin et al., Transobturator Subvesical Mesh. Tolerance and short-term results of a 103 case continuous series, Gynecologie Obstetrique & Fertilite, vol. 31, Issue 1, pp. 14-19 (Jan. 2003).

Farnsworth, B.N., Posterior Intravaginal Slingplasty (Infracoccygeal Sacropexy) for Sever Posthysterectomy Vaginal Vault Prolapse—A Preliminary Report on Efficacy and Safety, Int Urogynecology J, vol. 13, pp. 4-8 (2002).

Fidela, Marie R. et al., Pelvic Support Defects and Visceral and Sexual Function in Women Treated With Sacrospinous Ligament Suspension and Pelvic Reconstruction, Am J Obstet Gynecol, vol. 175, n. 6 (Dec. 1996).

Flood, C.G. et al., Anterior Colporrhaphy Reinforce With Marlex Mesh for the Treatment of Cystoceles, International Urogynecology Journal, vol. 9, pp. 200-204 (1998).

Guner, et al., Transvaginal Sacrospinous Colpopexy for Marked Uterovaginal and Vault Prolapse, Inter J of Gynec & Obstetrics, vol. 74, pp. 165-170 (2001).

Julian, Thomas, The Efficacy of Marlex Mesh in the Repair of Sever, Recurrent Vaginal Prolapse of the Anterior Midvaginal Wall, Am J Obstet Gynecol, vol. 175, n. 6, pp. 1472-1475 (Dec. 1996).

Karram, Mickey M. et al., Chapter 19 Surgical Treatment of Vaginal Vault Prolapse, Urogynecology and Reconstructive Pelvic Surgery, (Walters & Karram eds.) pp. 235-256 (Mosby 1999).

Lichtenstein, Irving L. et al, The Tension Free Hernioplasty, The American Journal of Surgery, vol. 157 pp. 188-193 (Feb. 1989).

Marchionni, Mauro et al., True Incidence of Vaginal Vault Prolapse—Thirteen Years of Experience, Journal of Reproductive Medicine, vol. 44, n. 8, pp. 679-684 (Aug. 199).

Marinkovic, Serge Peter et al., Triple Compartment Prolapse: Sacrocolpopexy With Anterior and Posterior Mesh Extensions, Br J Obstet Gynaecol, vol. 110, pp. 323-326 (Mar. 2003).

Migliari, Roberto et al., Tension-Free Vaginal Mesh Repair for Anterior Vaginal Wall Prolapse, Eur Urol, vol. 38, pp. 151-155 (Oct. 1999).

Migliari, Roberto et al., Treatment Results Using a Mixed Fiber Mesh in Patients With Grade IV Cystocele, Journal of Urology, vol. 161, pp. 1255-1258 (Apr. 1999).

Moir, J. Chassar et.al., The Gauze-Hammock Operation, The Journal of Obstetrics and Gynaecology of British Commonwealth, vol. 75 No. 1, pp. 1-9 (Jan. 1968).

Morley, George W. et al., Sacrospinous Ligament Fixations for Eversion of the Vagina, Am J Obstet Gyn, vol. 158, n. 4, pp. 872-881 (Apr. 1988).

Nicita, Giulio, A New Operation for Genitourinary Prolapse, Journal of Urology, vol. 160, pp. 741-745 (Sep. 1998).

Paraiso et al., Laparoscopic Surgery for Enterocele, Vaginal Apex Prolapse and Rectocele, Int. Urogynecol J, vol. 10, pp. 223-229 (1999).

Petros, Peter E. Papa, Vault Prolapse II; Restoration of Dynamic Vaginal Supports by Infracoccygeal Sacropexy, An Axial Day-Case Vaginal Procedure, Int Urogynecol J. vol. 12, pp. 296-303 (2001).

Richter, K. Massive Eversion of the Vagina: Pathogenesis, Diagnosis and Therapy of the "True" Prolapse of the Vaginal Stump, Clin obstet gynecol, vol. 25, pp. 897-912 (1982).

Sullivan, Eugene S. et al., Total Pelvic Mesh Repair a Ten-Year Experience, Dis. Colon Rectu , vol. 44, No. 6, pp. 857-863 (Jun. 2001).

Swift, S.E., et al., Case-Control Study of Etiologic Factors in the Development of Sever Pelvic Organ Prolapse, Int Urogynecol J, vol. 12, pp. 187-192 (2001).

Weber, Anne M. et al., Anterior Vaginal Prolapse: Review of Anatomy and Techniques of Surgical Repair, Obstetrics and Gynecology, vol. 89, n. 2, pp. 311-318 (Feb. 1997).

Winters et al., Abdominal Sacral Colpopexy and Abdominal Enterocele Repair in the Management of Vaginal Vault Prolapse, Urology, vol. 56, supp. 6A, pp. 55-63 (2000).

Zacharin, Robert et al., Pulsion Enterocele: Long-Term Results of an Abdominoperineal Technique, Obstetrics & Gynecology, vol. 55 No. 2, pp. 141-148 (Feb. 1980).

Mouly, Patrick et al., Vaginal Reconstruction of a Complete Vaginal Prolapse: The Trans Obturator Repair, Journal of Urology, vol. 169, p. 183 (Apr. 2003).

Kettel, L. Michael et al., An Anatomical Evaluation of the Sacrospinous Ligament Colpopexy, Surg. Gynecol. Obstet., 168(4):318-22, Apr. 1989.

Flynn, B.J. et al., Surgical Management of the Apical Vaginal Defect, Curr. Opin. Uro . 12(4):353-58, Jul. 2002.

Buller, J.L. et al., Uterosacral Ligament: Description of Anatomic Relationships to Optimize Sergical Safety, Obstet. Gynecol. 97:873-79, 2001.

Brochure, "GPS for Pelvic Floor Repair," Gynecare Prolift, 6 pages, 2005.

Greene, Frederick, "Repair of Rectal Prolapse Using a Puborectal Sling Procedure," Arch Surg; vol. 118, pp. 398-401 (Apr. 1983).

Shafik, Ahmed, "Puborectoplasty, New Technique for the Repair of Fecal Incontinence," Dig. Surg. 1991; 8: pp. 182-86.

McMahan et al., Rectal prolapse. An update on the rectal sling procedure,: Am Surg., vol. 53, No. 1, pp. 37-40, 1987.

O'Rourke D. et al., "A puborectal sling in the management of anal incontinence and rectal prolapse," Aust N Z J Surg., vol. 55, No. 5, pp. 493-495, 1985.

O'Rourke D. et al., "An anorectal sling in the treatment of rectal prolapse and incontinence," Aust N Z J Surg., vol. 44, No. 2, pp. 144-146, 1974.

* cited by examiner

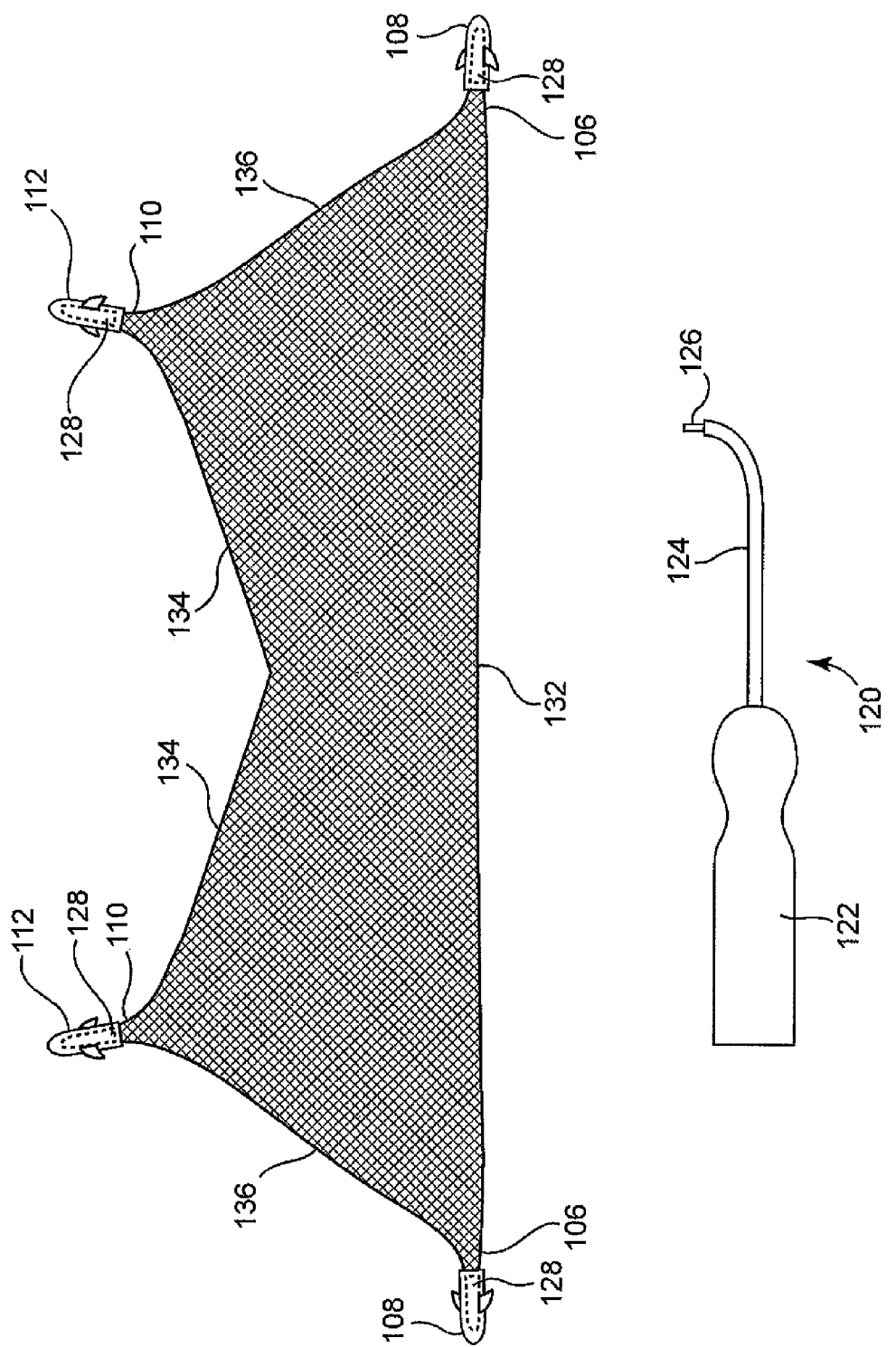

SURGICAL ARTICLES AND METHODS FOR TREATING PELVIC CONDITIONS

PRIORITY CLAIM

This application claims benefit from International Application No. PCT/US2007/022689, which was filed on 26 Oct. 2007, which in turn claims priority to U.S. Provisional Application Ser. No. 60/863,049, filed Oct. 26, 2006, entitled "MESH IMPLANTS FOR THE TREATMENT OF LEVATOR ANI MUSCLE DEFECTS AND FECAL INCONTINENCE"; and U.S. Provisional Application Ser. No. 60/947,044, filed Jun. 29, 2007, entitled "PELVIC FLOOR TREATMENTS AND ASSOCIATED IMPLANTS", which applications are incorporated herein by reference in their entirety.

FIELD OF THE INVENTION

The invention relates to apparatus and methods for treating pelvic conditions by use of a pelvic implant to support pelvic tissue. The pelvic conditions include conditions of the female or male anatomy, and specifically include treatments that involve supporting levator muscle, such as to treat female or male fecal incontinence, among other conditions.

BACKGROUND

Pelvic health for men and women is a medical area of increasing importance, at least in part due to an aging population. Examples of common pelvic ailments include incontinence (fecal and urinary) and pelvic tissue prolapse (e.g., female vaginal prolapse). Urinary incontinence can further be classified as including different types, such as stress urinary incontinence (SUI), urge urinary incontinence, mixed urinary incontinence, among others. Other pelvic floor disorders include cystocele, rectocele, enterocele, and prolapse such as anal, uterine and vaginal vault prolapse. A cystocele is a hernia of the bladder, usually into the vagina and introitus. Pelvic disorders such as these can result from weakness or damage to normal pelvic support systems.

Pelvic implants, sometimes referred to as slings, hammocks, have been introduced for implantation in the body to treat pelvic conditions such as prolapse and incontinence conditions. See, for example, commonly assigned U.S. Pat. Nos. 6,382,214, 6,641,524, 6,652,450, and 6,911,003, and publications and patents cited therein. The implantation of these implants involves the use of implantation tools that create transvaginal, transobturator, supra-pubic, or retro-pubic exposures or pathways. A delivery system for coupling the sling ends to ends of elongate insertion tools, to draw sling extension portions through tissue pathways, is also included. Needles of the right and left hand insertion tools described in the above-referenced 2005/0043580 patent publication have a curvature in a single plane and correspond more generally to the BioArc™ SP and SPARC™ single use sling implantation tools sold in a kit with an elongated urethral sling by American Medical Systems, Inc.

One specific area of pelvic health is trauma of the pelvic floor, e.g., of the levator ("levator ani") or coccygeus muscle (collectively the pelvic floor). The pelvic floor is made up of the levator and coccygeus muscles, and the levator is made up of components that include the puborectalis muscle, the pubococcygeus muscle, and the iliococcygeous muscle. For various reasons, the levator may suffer weakness or injury that can result in various symptoms such as prolapse, incontinence, and other conditions of the pelvis.

SUMMARY

The invention relates to methods of treating pelvic conditions, especially by supporting levator tissue. Levator defects (weakness or injury) can affect any portion of the levator, and can be especially common in the pubic portion of the levator ani, including the pubococcygeus and puborectalis muscles. Such defects are relatively common, for instance, in women with vaginal prolapse. Defects can also be present at the iliococcygeus muscle. Still other defects are in the form of a paravaginal defect, such as avulsion of the inferiomedial aspects of the levator ani from the pelvic sidewall; avulsion can refer to tissue being detached from the pubic bone, and may precede prolapse conditions. Another levator defect is levator ballooning, which refers to distension of levator muscles.

A different levator defect is a defect of the levator hiatus, which can reduce the stability of the pelvic floor and may result in sexual dysfunction, defecatory dysfunction, rectal prolapse, and fecal incontinence. Levator hiatus is also believed to play a significant role in the progression of prolapse. Embodiments of methods of the invention can address any of the conditions, as well as related conditions and symptoms.

The present patent application describes pelvic implants and methods for treating pelvic conditions by treating defects of the pelvic floor (coccygeus or levator), such as weakness or injury, or by otherwise supporting levator muscle. Useful methods can involve methods and implants that can restore natural pelvic floor anatomy using an implant (e.g., graft) in the form of a hammock, sling, and the like, to augment injured, weakened, or attenuated levator musculature. The levator musculature or "levator ani" can include the puborectalis, pubococcygeus, iliococcygeus.

Embodiments of implants useful according to the invention can be of a size and shape to address a desired pelvic floor condition, generally of a size and shape to conform to levator tissue, optionally to additionally contact or support other tissue of the pelvic region such as the anal sphincter, rectum, perineal body, etc. The implant can be of a single or multiple pieces that is or are shaped overall to match a portion of the levator, e.g., that is circular, oblong trapezoidal, rectangular, that contains a combination of straight, angled, and arcuate edges, etc. The implant may include attached or separate segments that fit together to extend beside or around pelvic features such as the rectum, anus, vagina, and the like, optionally to attach to the feature.

An implant (e.g., fecal sling) can be a continuous or a non-continuous sling, and can include one or multiple pieces or segments, e.g., an integral continuous implant or an assembly of segments. A continuous implant may be substantially continuous between edges, to be placed over a substantially continuous or level surface area of levator tissue. A non-continuous implant may include breaks or cuts that allow much of the implant to be placed on a level or continuous surface of levator tissue, with portions being formed to extend around tissue structure extending from or to the levator tissue, such as the anus, rectum, etc.

The implant can include a tissue support portion, which at least in part contacts levator tissue. Optionally, the implant can additionally include one or more extension portion that extends beyond the tissue support portion and to be secured to tissue of the pelvic region, for support of the tissue support portion.

Optionally, extension portions can include features such as a tissue fastener (e.g., self-fixating tip, soft tissue anchor, bone anchor, etc.), a sheath, a tensioning mechanism such as a suture, an adjustment mechanism, etc.

An implant, including a tissue support portion and optionally an extension portion, tissue fastener, etc., may optionally be coated with antimicrobial coatings to prevent infection or coatings to encourage ingrowth or inhibit rejection. For tissue support portions and extension portions, biocompatible materials are contemplated such as porcine dermis or meshes with growth factors.

A method as described herein may improve or treat a condition of the pelvic region, such as any of the pelvic conditions described. The method may support levator tissue, for treatment of prolapse; fecal incontinence; a torn, weakened, or damaged levator muscle (meaning any portion of the levator muscle); levator avulsion, levator ballooning, treatment to support a perineal body; a method of perineal body repair; a method of treating the levator hiatus by tightening or reducing the size of the levator hiatus; and combinations of one or more of these. The method may also be more general, as a treatment of more general conditions such as urinary continence, that is believed to be caused by or contributed to by a weakened levator.

The method may be prophylactic or medically necessary. A prophylactic treatment may be a preventative treatment for potential disease or condition that does not yet exist but that may be likely to exist. For example preventative treatment may be useful upon a grade one or two prolapse, for reinforcement of current prolapse repair, or post-partum. A medically necessary procedure may take place when a disease is present and in need of immediate treatment, such as in the case of perineal descent, fecal incontinence, reinforcement of current prolapse repair, and rectal prolapse.

An implant can be placed to contact pelvic tissue as desired, to support the tissue, such as levator tissue, and can optionally be secured to the tissue to be supported, e.g., by suturing. The implant can additionally be secured to tissue of the pelvic region for additional support, such as to tissue such as: sacrotuberous ligament; sacrospinous ligament; anococcygeal ligament ("anococcygeal body ligament"); periostium of the pubic bone (e.g., in a region of the ischial tuberosity); pubourethral ligament; ischial spine (e.g., at a region of the ischial spine); ischial tuberosity; arcus tendineus (used synonymously herein with the term "white line"), e.g., through a tissue path between levator ani muscle and obturator internus muscle and attached at the arcus tendineus; obturator internus muscle. Alternately, an extension portion of an implant can be extended through a tissue path that leads to an external incision such as: by passing through tissue of the obturator foramen to pass through an external incision at the inner thigh; passing above the pubic bone to exit at a suprapubic incision; passing in a posterior direction to an external perirectal or perianal incision, e.g., past the coccyx bone. As another alternative, an implant or extension portion of an implant can be attached to bone or fascia thereof, such as the sacrum or pubic bone, or fascia thereof.

According to exemplary methods, an implant can be introduced through an incision that allows access to levator tissue, optionally with some amount of dissection. The incision can be any of a variety of incisions that provide such access, such as a small external perirectal incision that can allow a tissue path to extend from the external perirectal incision to levator tissue; an external suprapubic incision; an external incision at an inner that can be used to pass a portion of an implant through an obturator foramen, a Kraske incision under the rectum; an incision at the perineum; and a vaginal incision.

An implant or a portion of the implant can be accessed or placed into position using the incision, to support tissue of the levator. Preferably the implant can be placed by dissecting a plane or region of dissection that includes the ischorectal fossa. Anatomical landmarks included with this region of dissection can include the ischial spine, the obturator internus, the arcus tendineus.

One embodiment of implant can be a synthetic or biologic implant having a tissue support portion. The tissue support portion can be sized and shaped to support levator tissue. The precise form can depend on the type of condition being treated. Certain embodiments of a tissue support portion may optionally include a segment or support for addressing levator hiatus opening, perineal descent, rectal prolapse, fecal incontinence, etc.

An implant may optionally but not necessarily include extension portions that extend to other tissue, e.g., in the pelvic region, sometimes referred to as "supportive tissue," to which the extension portion may be secured in a manner to allow the extension portion to support the tissue support portion. Also optionally, ends of extension portions can include a tissue fastening mechanism such as a self-fixating tip that can be secured to internal tissue of the pelvic region such as described elsewhere herein, including but not limited to tissue of: sacrotuberous ligament, sacrospinous ligament, periostium of the pubic bone (e.g., in a region of the ischial tuberosity), a region of the ischial spine, ischial tuberosity, pubourethral ligament, anococcygeal body ligament, and arcus tendineus; or through a tissue path between levator ani muscle and obturator internus muscle and attaching the extension portion at the arcus tendineus or obturator tissue (e.g., obturator internus), or passing through tissue of the obturator foramen.

The invention contemplates various methods of supporting levator tissue. Exemplary methods include steps that involve creating a single medial incision (a transvaginal incision or a perineal incision) or an incision near the rectum, anus, or perineum; and dissecting within a plane or region of dissection including the ischorectal fossa. An implant can be inserted to contact tissue of the levator, over a desired area. Optionally, the implant can be a single piece or multiple pieces or portions, and may include one or more tissue fasteners that can be secured to tissue in the pelvic region. An implant may include materials or components such as those used in the SPARC and Monarc systems (from American Medical Systems), include connectors for engagement between a needle of an insertion tool and an distal end of an extension portion, as well as helical, straight, and curved needles.

The invention furthermore contemplates embodiments of methods and apparatus for treating pelvic conditions that involve a single incision whereby the implant does not exit through another skin incision such as an abdominal or leg incision.

In one aspect, the invention relates to a method of supporting tissue of the pelvic floor, include levator tissue, coccygeus tissue, and combinations of these. The method includes: creating an incision that allows access to a region of inferior tissue of the pelvic floor, providing a pelvic implant comprising a tissue support portion, passing the implant through the incision and placing the tissue support portion at the region of the inferior tissue of the pelvic floor, and positioning the tissue support portion at the region of the inferior tissue in a manner to cause the tissue support portion to support the levator tissue.

In another aspect, the invention relates to pelvic implant for supporting tissue of the pelvic floor (e.g., levator tissue, coccygeus tissue, or combinations of these), and related surgical systems and kits. The implant includes a tissue support portion bounded by: an anterior side capable of extending from an anterior region of the pelvic region to a region of tissue of the medial pelvic floor, the anterior region selected from a region of the obturator foramen, a region of the arcus tendineus, and a region of puborectalis muscle; a posterior side capable of extending from a posterior region of the pelvic region to a region of the medial pelvic floor, the posterior region selected from a region of the ischial spine, an ischial tuberosity, a sacrospinous ligament, a sacrotuberous ligament, and a sacrum, and a lateral end capable of extending from the anterior region to the posterior region. The tissue support portion can be located at a region of levator tissue.

In another aspect the invention relates to a method of treating a pelvic condition by supporting tissue of the pelvic floor. The method includes: providing an implant comprising a tissue support portion and a tissue fastener, creating an incision that allows access to tissue of the pelvic floor, placing the tissue support portion in contact with tissue of the pelvic floor, and securing the tissue fastener to tissue of the pelvic region.

BRIEF DESCRIPTION OF DRAWINGS

Other features and advantages of the present invention will be seen as the following description of particular embodiments progresses in conjunction with the drawings. Drawings are schematic and not to scale.

FIG. 5A illustrates an embodiment of a kit comprising an implant as described and an insertion tool.

FIG. 8A illustrates an embodiment of incision as described.

DETAILED DESCRIPTION

Figure 1:
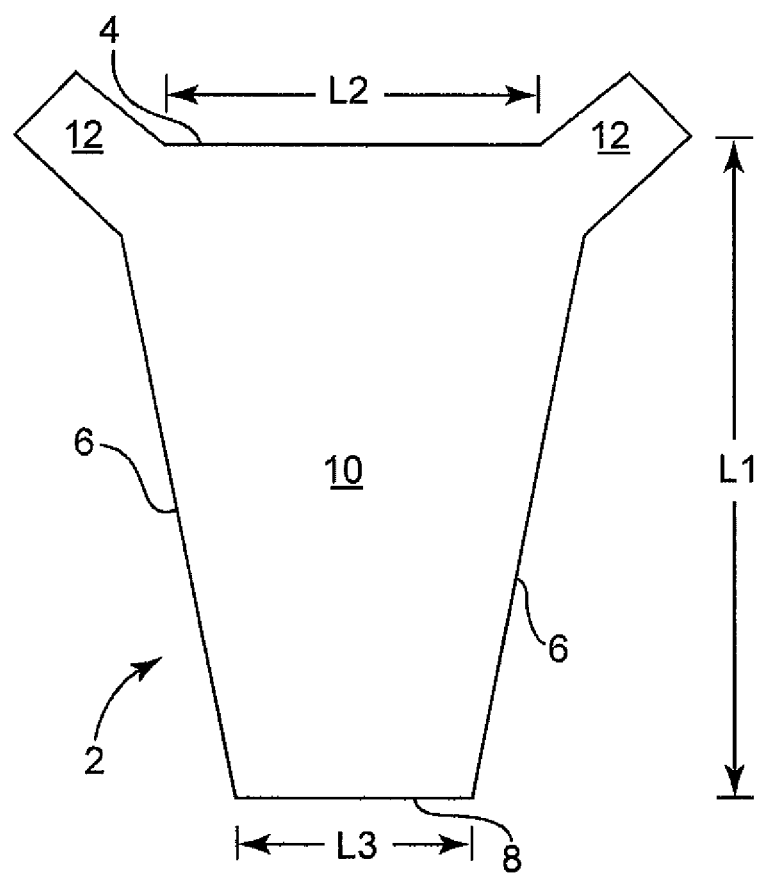
FIG. 1 illustrates an embodiment of an implant as described.

The following description is meant to be illustrative only and not limiting. Other embodiments of this invention will be apparent to those of ordinary skill in the art in view of this description.

The invention relates to surgical instruments, assemblies, and implantable articles for treating pelvic floor disorders such as prolapse, incontinence (urinary and fecal incontinence), conditions of the perineal body, conditions of levator muscle (such as a component of levator muscle), conditions of the levator hiatus, and combinations of two or more of these. According to various embodiments, a surgical implant can be used to treat a pelvic condition, wherein the method includes placing an implant in a manner that support tissue of the pelvic floor, including one or more of levator muscle and coccygeus muscle, in males or females. Various aspects of the invention are described as embodied by features of surgical implants, surgical tools, surgical systems, surgical kits, and surgical methods, useful for implants and for installing implants.

Defects of the pelvic floor, such as levator muscle distension or ballooning, may have a significant effect on perineal body descent and acute, potential, impending, or future pelvic prolapse, as well as prolapse recurrence. One embodiment of the invention involves methods by which tissue of the pelvic floor (e.g., levator muscle, coccygeus muscle) can be supported to reduce this distension. This embodiment involves placing various materials subcutaneously against levator or coccygeus muscle; the placement can be made by any incision and dissection route, but particular methods involve incisions in the perirectal, perianal, and perineal regions and not necessarily by use of a transvaginal incision. (According to other embodiments, an implant can be placed tranvaginally.)

According to certain embodiments of the invention, tissue of the pelvic floor can be supported by an implant in the form of a mesh or biologic sling, hammock, or the like, similar to some of those that have been previously to treat pelvic conditions such as forms of urinary incontinence, prolapse, fecal incontinence, etc., in men and women.

Other possible support mechanisms can be useful as well, other than those similar to such conventional pelvic implants, which may be considered "static." Examples of other support structures (i.e., "implants") include structures that are dynamic and not static. A dynamic implant can exhibit the ability to change after being implanted in a manner that can allow a dynamic function, such as dynamic support. The degree of support may be changed or adjusted at different stages of a disease or condition.

Examples of alternate support mechanisms (static or non-static) include but are not limited to: bulking agents (collagen, saline, silicone, etc.), expandable foam/insulation to fill volume, pillows filled with saline, silicone, or the like, that could be deflated and inflated to aid in defecation, sponges that could be combined with growth factors to facilitate ingrowth or used along to fill space.

Embodiments of methods that do not include vaginal dissection may be easier to perform and reduce risk and tissue trauma to the patient. This repair may be done during or after performing other treatments of the pelvic floor, such as to treat vaginal prolapse (e.g., vault prolapse, enterocele, rectocele, cystocele, etc.), may reduce the recurrence rate of vaginal prolapse (e.g., as addressed by products such as the Apogee™ and Perigee™ prolapse products from American Medical Systems, and similar products), and may provide an overall improvement when used in combination with or after other prolapse repair procedures. Alternately, procedures of the invention may be used prophylactically to prevent future prolapse. The procedures may be performed before, after, or concurrently with a hysterectomy, to potentially prevent or reduce the possibility or severity of subsequent prolapse. In other embodiments, a method as described may be useful following a prostatectomy or bladder removal (due to cancer), again to potentially prevent or reduce the possibility or severity of subsequent pelvic conditions.

Aspects of the invention relate to the use of an implant (e.g., polypropylene mesh), surgically implanted to support the levator muscles to reduce levator muscle distension, or to otherwise repair levator tissue. Techniques can involve delivering an implant (e.g., a mesh) to tissue of the levator and securing it into place to support the levator tissue. These procedures and devices involve placing an implant subcutaneously against the levator muscle (i.e., below or inferior to the levator muscle). This can be done transvaginally, but also can be done with an external incision in the perineal area (of the male or female anatomy), perirectal area, or with other incision locations.

In certain embodiments, the implant (either the tissue support portion or an extension portion) can also be secured to other tissue, i.e., "supportive tissue," of the pelvic region, to support the tissue support portion. Exemplary supportive tissue is described herein, for example at FIG. 6 and related text, and is described at other portions of the present description. Supportive tissue includes, tissue at an anterior location such as at the obturator foramen or arcus tendineus, or at a posterior location such as a region of the ischial spine or at a sacrospinous ligament.

The implant can be attached to such supportive tissue directly or by use of a tissue fasteners (e.g., anchors such as bone anchors, soft tissue anchors, self-fixating tips, tissue clamps, etc.) A tissue fastener may be attached to a tissue support portion or to an extension portion of an implant, and may be attached to either of these directly or by a connective suture. According to the latter, a tissue fastener can be placed and then material of the implant (e.g., mesh) may be guided along the suture lines as a track or guide to be tacked into place.

Embodiments of certain implants of can be of materials and designs that will be the same as or similar to implants conventionally useful for other treatments of the pelvic region. An implant can include a tissue support portion (or "support portion") that can be used to support pelvic tissue, especially tissue of levator muscle. During use, the tissue support portion is typically placed in contact with tissue to be supported, e.g., levator tissue, and optionally in addition, to surrounding tissue such as tissue of the rectum, tissue of a perineal body, tissue of the external anal sphincter, to support one or more of these. Also optionally the tissue support portion can be attached to such tissue, for example as with a suture, biological adhesive, etc.

Embodiments of implants can optionally include one or more extension portions (also sometimes referred to as "end portions" or "arms") attached to the tissue support portion. Extension portions are pieces of material, for example elongate pieces of material, that extend from the tissue support portion and either are or can be connected to the tissue support portion, and are useful to attach to or pass through anatomical features in the pelvic region to provide support for the tissue support portion and the supported tissue. One or multiple (e.g., one, two, or four) extension portions can extend from the tissue support portion as elongate "ends," "arms," or "extensions," useful to attach to tissue in the pelvic region, such as by extending through a tissue path to an internal anchoring point as described herein. Optionally, according to alternate embodiments of the invention, the extension portion may pass through tissue of the pelvic region and to an external incision.

Embodiments of exemplary implants that may be useful as discussed herein can include a tissue support portion and no extension portions. Other embodiments can include one, two, three, or more extension portions attached to a tissue support portion. An exemplary urethral sling can be an integral mesh strip or hammock with supportive portions consisting of or consisting essentially of a central support portion and zero, one, or two extension portions.

An implant may include portions or sections that are synthetic or of biological material (e.g., porcine, cadaveric, etc.), and that may be resorbable or non-resorbable. Extension portions may be, e.g., a synthetic mesh such as a polypropylene mesh. The tissue support portion may be synthetic (e.g., a polypropylene mesh) or biologic.

The implant, either or both of the tissue support portion or an extension portion, may comprise variable weave meshes with varying elasticities such as a mesh that is highly elastic around the anus to allow stool to pass.

Some example of commercially available materials may include Marlex™ (polypropylene) available from Bard of Covington, R.I., Prolene™ (polypropylene) and Mersilene (polyethylene terephthalate) Hernia Mesh available from Ethicon, of New Jersey, Gore-TeX™ (expanded polytetrafluoroethylene) available from W. L. Gore and associates, Phoenix, Ariz., and the polypropylene sling material available in the SPARC™ sling system, available from American Medical Systems, Inc. of Minnetonka, Minn. Commercial examples of absorbable materials include Dexon™ (polyglycolic acid) available from Davis and Geck of Danbury, Conn., and Vicryl™ available from Ethicon.

Dimensions of an implant can be as desired and useful for any particular installation procedure, treatment, patient anatomy, to support a specific tissue or type of tissue, and to extend to a desired location of internal supportive tissue or an external incision. Exemplary dimensions can be sufficient to allow the tissue support portion to contact tissue of the levator, coccygeus, rectum, external anal sphincter, etc., or any desired portion of one or more of these. Optionally, one or more extension portion can extend from the tissue support portion to a desired internal or external anatomical location to allow the extension portion to be secured to anatomy of the pelvic region, to support the tissue support portion.

Dimensions of extension portions according to the invention can allow the extension portion to reach between a tissue support portion placed to support tissue of the pelvic floor (at an end of the extension portion connected to the tissue support portion) and a location at which the distal end of the extension portion attaches to pelvic tissue, or may optionally pass through an external incision.

An implant can be of a single or multiple pieces that is or are shaped overall to match a portion of the levator, e.g., that is completely or partially circular, trapezoidal (non-symmetric or symmetric), rectangular, rhomboidal, etc. The implant may be multiple pieces to fit beside or around pelvic features such as the rectum or anus. Alternately, the implant may be irregular (while optionally symmetrical) to reach different areas of the levator.

To contact tissue of the pelvic floor, an implant (e.g., fecal sling) can be a continuous or a non-continuous sling, and of one or multiple pieces or segments. A continuous implant may be substantially continuous between edges, to be placed over a level surface area of levator tissue. A non-continuous implant may include breaks or cuts that allow much of the implant to be placed on a level surface of levator tissue, with portions being formed to extend around tissue structure extending from or to the levator tissues, such as the anus, rectum, etc.

An embodiment of a non-continuous sling may be designed to cover or contact area of the levator, coccygeus, or both, and also reach around to contact a posterior side of the rectum or external anal sphincter. For example, a portion of an implant could attach to the lateral sides of the external anal sphincter and extend toward or in the direction of the obturator foramen, or any other suspensory structure (e.g., supportive tissue), but need not engage tissue of the obturator foramen directly. In this embodiment, the tissue support portion of the implant need not necessarily be directly under the anus to provide the corrective action for fecal incontinence. An advantage to of this approach is to allow the anus to expand unrestricted to facilitate normal rectal function and may give the levator plate (or plates) the support necessary to be leveraged.

Embodiments of implants can include a segment that is located anterior to the anus, such as in contact with levator tissue or tissue of the perineal body, anterior to the anus. Alternate implants may be designed to replace the perineal muscle or attach to the superior portion of the external sphincter. The various embodiments disclosed herein are also applicable to men and can be implanted via an incision in the perineal floor (see attached figures).

An implant, e.g., at a tissue support portion or at a distal end of an extension portion, can optionally include a tissue fastener that attaches to tissue of the pelvic region. The tissue fastener can be, e.g., a soft tissue anchor, a self-fixating tip, a biologic adhesive, a tissue clamp, opposing male and female connector elements that securely engage when pushed together, or any other device to secure a distal end of an extension portion to tissue of the pelvic region. Exemplary tissue fasteners are discussed, e.g., in PCT/SU2007/014120 "Surgical Implants, Tools, and Methods for Treating Pelvic Conditions, filed Jun. 15, 2007; the entirety of which is incorporated herein by reference. The implant may also have extension portions that do not include a tissue fastener at a distal end thereof, for example if the distal end is designed to be secured to tissue by other methods (e.g., suturing), or is intended to pass through a tissue path ending in an external incision.

An extension portion can be attached to any desired tissue of the pelvic region, or passed through a desired tissue path to an external incision. To attach an extension portion to tissue, a tissue fastener can optionally be attached at the distal end of the extension portion. During installation of the implant, the tissue fastener can be attached to any desired tissue, e.g., supportive tissue, many examples of which are described herein. Supportive tissue can be fibrous tissue such as a muscle (e.g., obturator foramen, especially the obturator internus; obturator externus; ligament such as the sacrotuberous ligament, sacrospinous ligament, or surrounding tissue; a tendon such as the arcus tendineus or surrounding tissue; or tissue at or near the ischial spine (i.e., at a region of the ischial spine) such as the ischial tuberosity.

A length of an extension portion (extended through any tissue path) can optionally be fixed or adjustable, allowing a surgeon to alter the length of an extension portion before, during, or after implantation. On the other hand, adjustment and tensioning mechanisms can also be excluded from embodiments of implants or from particular extension portions, e.g., superior extension portions that will attach to an obturator foramen, or extension portions that will be placed at a tissue path extending to an external incision.

A length of an extension portion can be sufficient to allow the distal end to reach desired tissue within or external to the pelvic region, e.g., from about 1 centimeter (cm) to about 5 centimeters. A width of the extension portion can be as desired, such as within the range from about 1 to 1.5 centimeters.

A "self-fixating tip" in general can be a structure connected to a distal end of an extension portion that can be implanted into tissue in a manner that will maintain the position of the self-fixating tip and support the attached implant. Exemplary self-fixating tips can also be designed to engage an end of an insertion tool (e.g., elongate needle, elongate tube, etc.) so the insertion tool can be used to push the self-fixating tip through tissue for implantation. The self-fixating tip may engage the insertion tool at an internal channel of the self-fixating tip, at an external location such as at a cylindrical base, or at a lateral extension, as desired. Exemplary self-fixating tips are described, for example, in PCT/US2007/004015 "Surgical Articles and Methods for Treating Pelvic Conditions," filed Feb. 16, 2007, the entirety of which is incorporated herein by reference.

A self-fixating tip can be made out of any useful material, generally including materials that can be molded or formed to a desired structure and connected to or attached to an end of an extension portion of an implant. Useful materials can include plastics such as polyethylene, polypropylene, and other thermoplastic or thermoformable materials, as well as metals, ceramics, and other types of biocompatible and optionally bioabsorbable or bioresorbable materials. Exemplary bioabsorbable materials include, e.g., polyglycolic acid (PGA), polylactide (PLA), copolymers of PGA and PLA.

A self-fixating tip may be of any form that can be inserted into tissue of a pelvic region, and that will thereafter be retained in the tissue. Exemplary self-fixating tips can include one or more lateral extensions that can increase the force required to remove the self-fixating tip from tissue after insertion into the tissue, i.e. the "pullout force." At the same time, the lateral extensions can be designed to exhibit a reduced or relatively low "insertion force," which is the amount of force used to insert the self-fixating tip into tissue. The self-fixating tip can be designed to be essentially permanently placed upon insertion into tissue, with the single exception that if absolutely necessary to provide desired placement of the self-fixating tip or an attached implant, the self-fixating tip may be removed by a surgeon during an implantation procedure. The self-fixating tip, and all components of the self-fixating tip, can be of combined form and dimensions to result in these functional features.

According to exemplary embodiments, a self-fixating tip can have structure that includes a base having a proximal base end and a distal base end. The proximal base end can be connected (directly or indirectly, such as by a connective suture) to a distal end of an extension portion, or directly to a tissue support portion of an implant. The base extends from a proximal base end to a distal base end and can optionally include an internal channel extending from the proximal base end at least partially along a length of the base toward the distal base end. The optional internal channel can be designed to interact with (i.e., engage) a distal end of an insertion tool to allow the insertion tool to be used to place the self-fixating tip at a location within pelvic tissue of the patient.

Alternate embodiments of self-fixating tips do not require and can exclude an internal channel for engaging an insertion tool. These alternate embodiments may be solid, with no internal channel, and may engage an insertion tool, if desired, by any alternate form of engagement, such as, for example, by use of an insertion tool that contacts the self-fixating tip at an external location such as by grasping the base (on a side or at the face of the proximal base end) or by contacting a lateral extension.

Embodiments of self-fixating tips also include one or more lateral extension extending laterally (e.g., radially) from the base, such as from a location between the proximal end and the distal end, from a location at the distal base end, or from a location at the proximal base end.

A self-fixating tip can be connected to an implant, such as at an extension portion of an implant, or to a tissue support portion, in any fashion, directly by any attachment mechanism, or indirectly such as through an attachment structure such as a suture. A connection can be based on a mechanical structure, by adhesive, by a connecting suture, or by an integral connection such as by injection molding or "insert" molding (also, "overmolding") as described U.S. Publication No. 2006-0260618-A1, incorporated herein by reference. According to that description a thermoplastic or thermosetting polymer material can be insert molded or injection molded at an end of a mesh extension portion of an implant, e.g., directly to the mesh. By this method, a molded polymer can form a self-fixating tip at an end of an extension portion. The self-fixating tip can be as described herein, for example, including lateral extensions and an internal channel.

An example of an implant is shown at FIG. 1. Implant 2, including tissue support portion 10, is generally in the form of a symmetric trapezoid (with added extension portions 12), but may alternately be a symmetric rectangle, a rhombus, a square, a non-symmetric trapezoid, an oblong rectangle, or the like. Two extension portions 12 are located at corners that connect wide end 4 to sides 6. Sides 6 extend and terminate at narrow end 8. Tissue fasteners (not shown) can be placed at extension portions 12. In use, an extension portion can be attached to tissue of the pelvic region; for example one of tissue extension portions 12 can be attached to tissue in a posterior location such as a region of the ischial spine, sacrospinous ligament, ischiorectal fossa, or iliococcygeous muscle; the other extension portion can be attached at an anterior location such as at tissue of the obturator foramen, e.g., the obturator internus muscle near the inferior pubic ramus, tissue of the arcus tendineus, etc. This places long end 4 at a lateral position. Tissue support portion 10 extends medially below levator tissue and short end 8 becomes located at a medial position. Short end 8 can be placed, for example, under the rectum. When so placed the implant extends from lateral positions between a region of the ischial spine or sacrospinous ligament, to a region of the obturator foramen or arcus tendineus, with tissue support portion 10 in contact with levator tissue, and with short end 8 at a medial position, e.g., near the rectum, optionally under the anococcygeal body ligament.

Lengths of the ends and sides can be as desired to allow for this placement. For example, length L1 can be in the range from 6 to 12 centimeters, such as from 7 to 10 centimeters. Length L2 of wide end 4 (not including extension portions 12) can be, e.g., from 3 to 5 centimeters. Length L3 of narrow end 8 can be, e.g., from 2 to 3 centimeters.

According to methods of the invention, implant 2 can be inserted through a medial incision, such as at the perineum, and placed as described, below levator tissue. Implant 2 is placed on one side of the pelvic floor to support substantially one side or half of levator muscle. A second implant of the same design can be placed to support the contralateral side, according to the same method. In this embodiment of implant and method, two separate implants are used, one below each side of the levator muscle, with short ends extending to a medial location. Preferably, the implants are also located below the superficial transverse perineal muscle. The short ends may overlap or be secured to each other or to tissue of the pelvic region, e.g., by a suture or other securing means such as adhesive, staples, etc.

Figure 2:
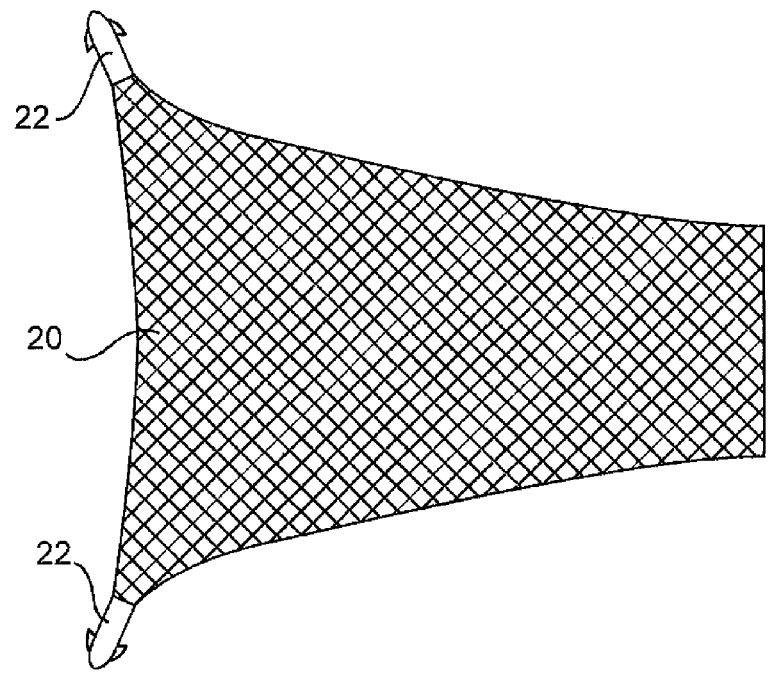
FIG. 2 illustrates an embodiment of an implant as described.

In FIG. 1, implant 12 can be a synthetic or a biologic material. FIG. 2 shows an example of an implant, 20, of synthetic mesh. Self-fixating tips 22 are located at corners of the implant (either with or in the absence of an extension portion). Again, implant 20 is designed for methods that use two opposing implants, one to support each side of the levator muscle.

Figure 3:
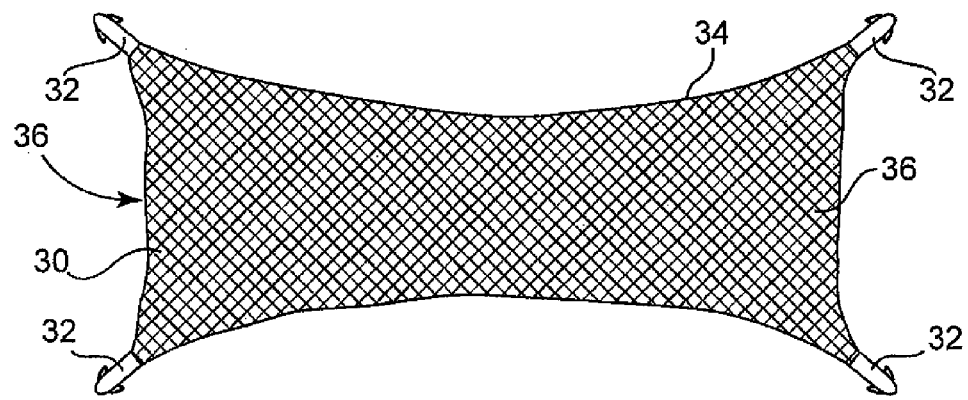
FIG. 3 illustrates an embodiment of an implant as described.

FIG. 3 illustrates an alternate implant, implant 30, which includes two opposing trapezoidally shaped portions of an implant, the opposing portions being connected integrally at the middle by a connection of narrow ends. Implant 30 may be integrally constructed or prepared from two implants of the type shown in FIG. 2. Implant 30 also includes self-fixating tips 32, which, in use, can be placed as described for extension portions 12 of implant 2. In use, narrow medial portion 34 of implant 30 can be placed medially, e.g., under the rectum. Lengths of wide ends 36 can be, e.g., from 4 to 5 centimeters. The width of implant 30 at narrow medial portion 34 can be, e.g., from 2 to 3 centimeters. The total length (the direction perpendicular to with at medial portion 34) can be, e.g., from 14 to 18 centimeters, e.g., from 15 to 17 centimeters.

Figure 4:
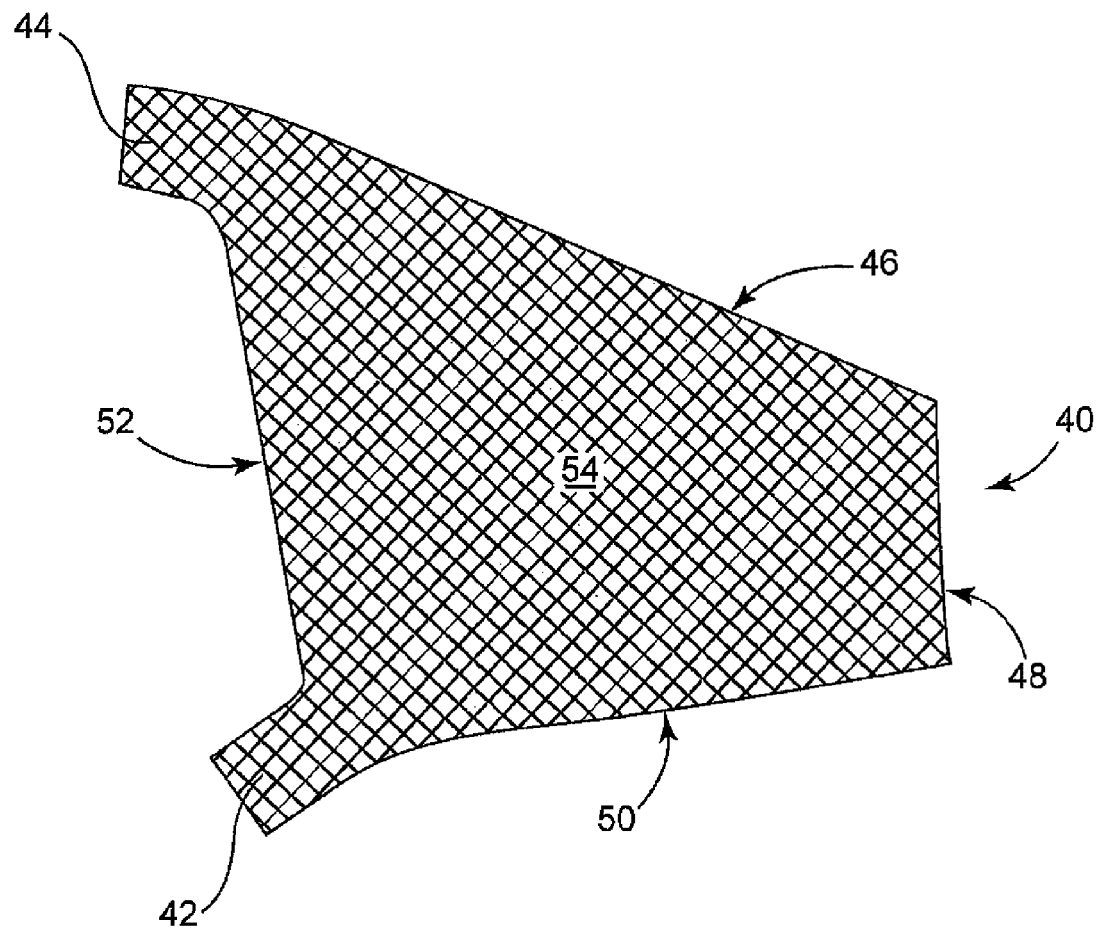
FIG. 4 illustrates an embodiment of an implant as described.

Another embodiment of an implant is shown at FIG. 4. Implant 40, including tissue support portion 54, is generally in the form of a non-symmetric trapezoid. Two extension portions, anterior extension portion 44 and posterior extension portion 42, are located at corners that connect lateral end 52 to anterior side 46 and posterior side 50. Anterior side 46 and posterior side 50 extend medially to medial end 48. Tissue fasteners (not shown) can optionally be placed at extension portions 42 and 44. In use, anterior extension portion 44 can be attached to tissue of the anterior pelvic region, for example tissue of the obturator foramen, e.g., the obturator internus muscle near the inferior pubic ramus, or at tissue of the arcus tendineus. Posterior extension portion 42 can be attached to tissue of the posterior pelvic region, such as in a region of the ischial spine, e.g., at a sacrospinous ligament, ischiorectal fossa, or iliococcygeous muscle. Lateral side 52 extends anteriorly to posteriorly at a lateral position, and medial end 48 becomes located at a medial position, for example, under the rectum. When so placed the implant extends from lateral positions between, e.g., a region of the ischial spine, and, e.g., a region of the obturator foramen, with tissue support portion 54 in contact with levator tissue, and with medial end 48 at a medial position, e.g., near the rectum, optionally under the anococcygeal body ligament. Overall, the implant can provide lateral support along the iliococcygeus muscle, and more central support along the pubococcygeus and puborectalis.

Lengths of the ends and sides can be as desired to allow for this placement. For example, a lateral end 52 can be, e.g., from 5 to 7 centimeters. A length of anterior side 46 can be can be in the range from 5 to 10 centimeters, such as from 6 to 9 centimeters. A length of posterior side 50 can be somewhat shorter, such as from 4 to 8 centimeters, or from 5 to 6 centimeters. Length of medial end 48 can be, e.g., from 2 to 3 centimeters.

In FIG. 4, implant 40 is of synthetic mesh, but can alternately be of a biologic material.

According to methods of the invention, implant 40 can be inserted through a medial incision (e.g., a perineal incision) and placed as described, below tissue of the pelvic floor such as coccygeus muscle or levator muscle. Implant 40 is placed below tissue of one side of the pelvic floor, to support substantially one side or half of the pelvic floor. A second implant of the same design (but in the form of a mirror image) can be placed to support the contralateral side of the pelvic floor, according to the same method. In this embodiment of implant and methods, two separate implants are used, one to support each side of the levator muscle, with medial ends extending to a medial location. Preferably, the implants are also located below the superficial transverse perineal muscle. The medial ends may overlap or be secured, e.g., by a suture or other securing means such as adhesive, staples, etc. In an alternate embodiment, two implants, 40, and a mirror image, can be connected at medial ends and used as a single implant.

An insertion tool can be used to install an implant. Various types of insertion tools are known, and these types of tools and modifications thereof can be used according to this description to install an implant. Examples of useful tools include those types of tools that generally includes a thin elongate needle that attaches to a handle; a handle attached to one end (a proximal end) of the needle; and a distal end of the needle adapted to engage a self-fixating tip that allows the needle to push the self-fixating tip through a tissue passage and insert the self-fixating tip within tissue of the pelvic region. (In alternate embodiments, a connector can be used in place of the self-fixating tip, the connector being able to engage a distal end of an insertion tool to allow the connector to be pushed or pulled through a tissue path leading to an external tissue incision.) This class of tool can be used with a self-fixating tip (or other form of connector) that includes an internal channel designed to be engaged by a distal end of an insertion tool.

Other general types of insertion tools will also be useful, but may engage a self-fixating tip (or connector) in a manner that does not involve an internal channel of a self-fixating tip. These alternate insertion tools may for example contact or grasp a proximal base end of a self-fixating tip in the absence of an internal channel extending from the proximal base end toward the distal base end, such as by grasping an external surface of the base. An alternate insertion tool may contact or grasp a side of the base, a lateral extension, or any other portion of the self-fixating tip or base, in a way that allows the insertion tool to hold the self-fixating tip and insert the self-fixating tip at a desired location within tissue of the pelvic region.

Exemplary insertion tools for treatment of incontinence and vaginal prolapse are described, e.g., in U.S. patent application Ser. Nos. 10/834,943; 10/306,179; 11/347,553; 11/398,368; 10/840,646; PCT application number 2006/028828; and PCT application number 2006/0260618; among others. Tools described in those patent documents are designed for placement of an implant in a pelvic region for the treatment of prolapse, male or female incontinence, etc. The tools of the above-referenced patent documents may be straight or may be curved in two or three dimensions, and may include, for example, a helical portion in three dimensions for placing an extension portion of an implant through a tissue path that passes from a region of the urethra, through an obturator foramen, to an external incision in the groin or inner thigh area. Other described insertion tools include a two or three-dimensional elongate needle that allows a user to place an extension portion of an implant through an external incision, e.g., at a suprapubic location or at a perianal or perirectal location.

Exemplary insertion tools for use according to the invention can be similar to or can include features of tools described in the above-referenced patent documents. For use according to embodiments of methods described herein, wherein an implant includes a self-fixating tip, those insertion tools may be modified to allow the insertion tool to be used to place a self-fixating tip at tissue within the pelvic region through a tissue path that does not extend to an external incision. The insertion tool can be designed, shaped, and sized, to include an elongate inserter or needle that may be straight or that may be curved in two or three dimensions, that can be inserted through a vaginal incision (for female anatomy), through a perineal incision (for male anatomy), or through any one of the other incisions described herein, and to extend from that incision to a pelvic tissue location for placement of a self-fixating tip.

Certain embodiments of insertion tools can be designed to reach through a vaginal incision, perineal incision, or other described incision, through an internal tissue path and to then extend through a second external incision, e.g., at the inner groin, thigh, abdominal area, suprapubic region, or perirectal or perianal region. Alternate tools can be sized and shaped to place a self-fixating tip at an internal location of the pelvic region, and do not need to be sufficiently long to extend from an incision to an external incision. The length can be only sufficient to reach from a vaginal or perirectal incision to an obturator foramen, region of the ischial spine, sacrospinous ligament, or other location of placing a self-fixating tip. Alternately, the length may be only sufficient to reach from a desired incision to a different muscle or tissue, such as a levator ani, coccygeous muscle, iliococcygeous muscle, arcus tendineus, etc., to place a self-fixating tip at one of those tissues.

According to an aspect of the invention, an implant can include one or multiple self-fixating tips at a tissue support portion or optionally at one or multiple ends of optional extension portions, and an implantation method can include placing the self-fixating tip or tips within tissue in the pelvic region to support the implant as the implant supports a type of pelvic tissue. The tissue can be a fibrous tissue such as a muscle (e.g., of the obturator foramen, obturator internus, obturator externus, levator ani, coccygeous, iliococcygeous), ligament (e.g., sacrospinous ligament), tendon (arcus tendineus), etc. Also preferably, but not as a requirement of the invention, a self-fixating tip can be oriented in a fibrous tissue to cause a major dimension (referred to herein as the "width") of a lateral extension to be oriented in a direction that is not parallel to the direction of the fibers.

To control the placement and degree of support of the implant relative to a tissue to be supported by the implant, the self-fixating tip can be inserted at a desired point of entry relative to the total area of the tissue, and, for tissues of sufficient thickness or depth, the self-fixating tip can be inserted to a selected depth.

A single example of a method according to the invention is a method of improving positioning of, or supporting, tissue of the pelvic floor or a portion thereof, by surgical implantation of an implant (e.g., a single, integral, optionally uniform, woven polymeric mesh strip) through an incision that allows access to the tissue of the pelvic floor (e.g., levator tissue, coccygeus tissue), such as a vaginal incision (for female anatomy), perineal (for male or female anatomy) incision, or another incision as described herein. Certain embodiments of these methods can advantageously involve only a single incision (a vaginal incision in a female or a perineal incision in a female or male) and can exclude the need for any additional incision.

Figure 5:
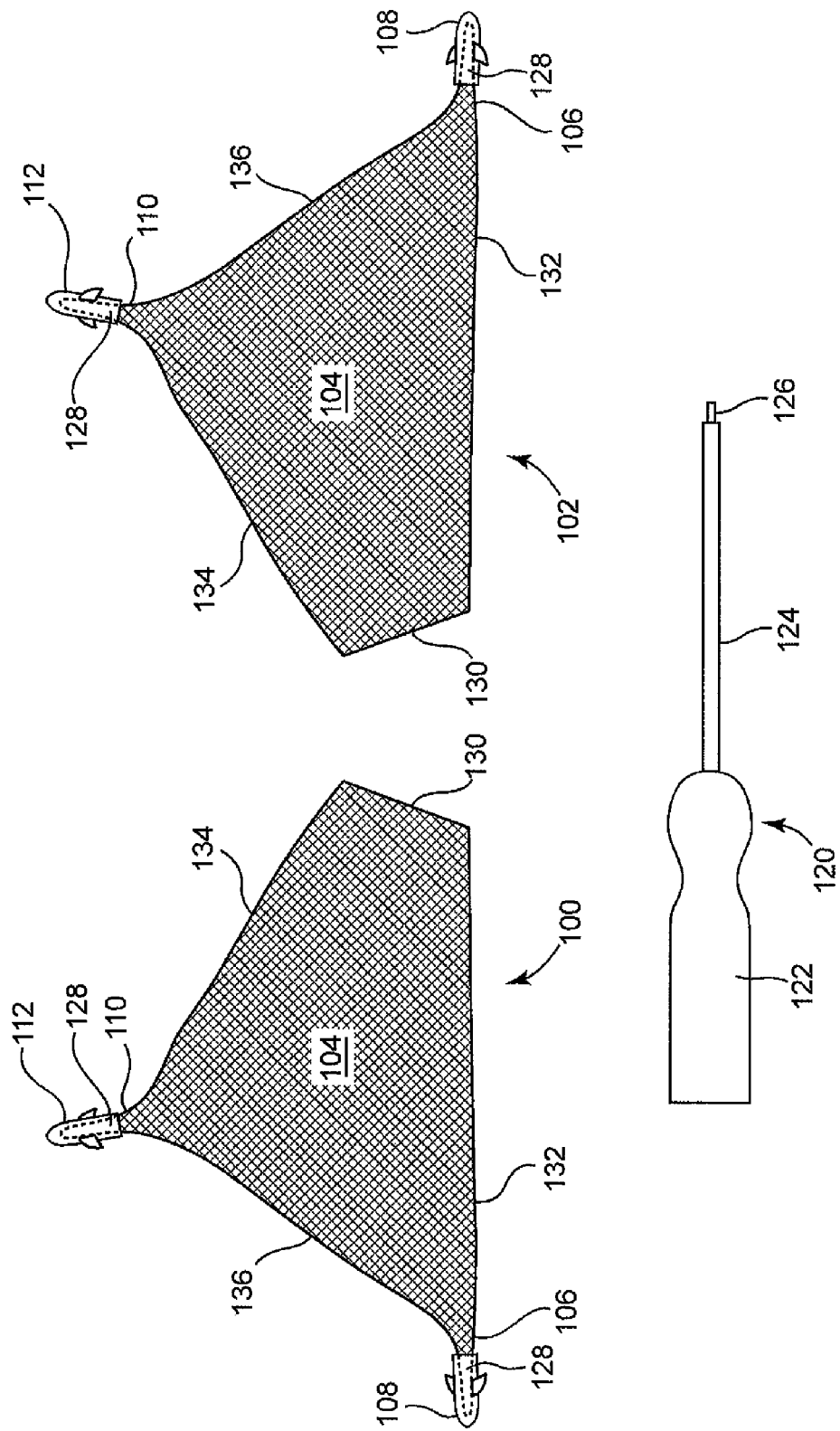
FIG. 5 illustrates an embodiment of a kit comprising an implant as described and an insertion tool.

An embodiment of a kit according to the invention, including an insertion tool and an implant, is shown at FIG. 5. Implant 100 can be installed to support tissue of the levator. Implant 100 is designed to support a portion of levator tissue, and implant 102 is designed to support a contralateral portion of levator tissue. Each implant includes a tissue support portion (104), an anterior extension portion (106) that includes a tissue fastener (108) in the form of a self-fixating tip. Each implant also includes a posterior extension portion (110) that includes a tissue fastener (112) in the form of a self-fixating tip. Sides and ends include: lateral ends 136, which can extend along a lateral portion of the levator, such as near the arcus tendineus between an anterior position and a posterior position; anterior sides 132 extending from medial end 130 to anterior extension portion 106; posterior sides 134 extending from medial end 130 to posterior extension portion 110; and medial end 130.

Tool 120 is also part of the kit. Tool 120 includes handle 122 connected to a proximal end of elongate needle 124. Distal end 126 is configured to engage internal channels or bores 128 (shown in dashed lines) of each of the tissue fasteners 108 and 112. Tool 120 is shown to have a straight needle portion 124, but could have a needle portion that is curved in two or three dimensions.

FIG. 5 shows two implants, 102 and 100, which are mirror images of each other in the form of non-symmetric trapezoids, as part of a kit. Alternate kits could include two implants of other shapes, e.g., as discussed herein, including a rectangle, symmetric trapezoid, square, or any of these general shapes, alternately with one or more of the straight edges being arcuate if desired. In other alternate kits, an implant can be in the form generally of the two implants connected (e.g., integrally or by a connection mechanism such as a suture) at medial ends 130. (See FIG. 5A.)

Optionally, according to various implant embodiments, such as implant 100 or 102, a material that forms any portion of a sling 100 may include one or more substances incorporated into the material or coated onto the material of the sling. Examples of substances may include, without limitation, drugs, hormones, antibiotics, antimicrobial substances, dyes, silicone elastomers, polyurethanes, radiopaque filaments or substances, position or length indicators, anti-bacterial substances, chemicals or agents, including any combinations thereof. A substance or material may be used to enhance treatment effects, reduce potential sling rejection by the body, reduce the chances of tissue erosion, allow or enhance visualization or location monitoring, indicate proper sling orientation, resist infection, or other provide other desired, useful, or advantageous effects.

Also with respect to any implant, such as implants 100, 102, or alternate embodiments, sling tension may be adjusted by a tension member such as a tensioning suture disclosed, for example, in U.S. Pat. No. 6,652,450. The tensioning suture may be constructed from a permanent or absorbable (i.e., bioresorbable or bioabsorbable) material. The tensioning member may be located along any portion of the implant such as a tissue support portion or extension portion.

Certain embodiments of the present invention are described with reference to supporting levator tissue and coccygeus tissue. Additionally, the invention is also useful for more specifically treating symptoms caused by weakened or damaged levator or coccygeus tissue, in both males and females. For example, embodiments of the present invention would be suitable for a variety of pelvic floor repairs or treatments, including pelvic organ prolapse repair, levator ballooning, a paravaginal defect such as levator avulsion, levator hiatus repair, fecal incontinence treatment, perineal body support, rectal support, levator tissue repair, etc.

Figure 6:
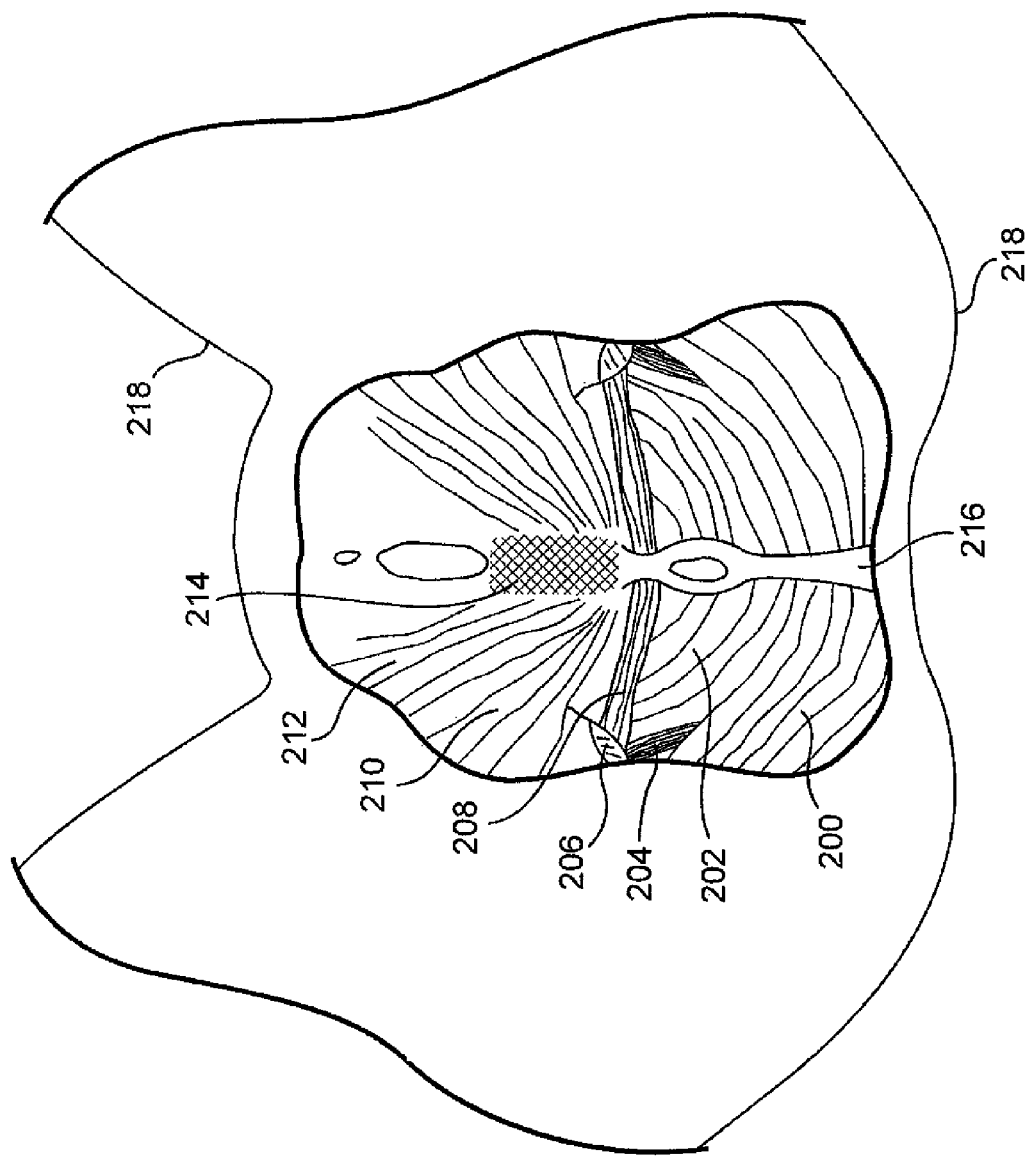
FIG. 6 illustrates anatomy of the pelvic region.

FIG. 6 shows anatomy relevant to methods and devices of embodiments of the invention. Referring to FIG. 6, illustrated is an view of inferior tissue at different levels of the pelvic region, including gluteus maximus 200, levator ani 202 (which includes the iliococcygeus muscle), sacrotuberous ligament 204, ischial tuberosity 206, superficial transverse perineal muscle 208, pubococcygeus muscle 210, puborectalis muscle 212, and perineal body 214. Epidermis 218 and coccyx 216 are shown for reference.

According to exemplary methods of the invention, a method of supporting levator or coccygeus tissue can include a step of creating an incision that allows access to a region of lower (inferior) levator or coccygeus tissue. Upon making the incision, some amount of dissection may be preferred or necessary. For example, placement of an implant may be performed with dissection of a plane or region of dissection that includes the ischorectal fossa. Anatomical landmarks included with this region of dissection can include the ischial spine, the obturator internus, the arcus tendineus.

An implant or a portion of an implant can be inserted through the incision or accessed through the incision. The implant can be as generally or specifically described herein, such as in any of FIGS. 1 through 4, 5, and 5A, including a tissue support portion, and optionally including one or multiple tissue fasteners optionally located at a corner of an implant or at a distal end of an optional extension portion. The implant can be passed through the incision and the tissue support portion is placed to support levator tissue, coccygeus tissue, or both, at an inferior region or inferior side thereof (i.e., "below" or inferior to tissue).

According to certain embodiments of the invention, the tissue support portion can also be located below (inferior to) the superficial transverse perineal muscle, to support this tissue as well. The tissue support portion can optionally be secured to levator tissue, tissue of the superficial transverse perineal muscle, or both. The tissue support portion is positioned at a region of inferior levator tissue in a manner to cause the tissue support portion to support levator tissue. Optionally the tissue support portion can be positioned below the rectum, attached to the rectum, or attached to the external anal sphincter.

Referring to FIG. 6, an embodiment of a method can include placing the implant, e.g., the tissue support portion or a distal end of an extension portion, into contact with supportive tissue selected from: sacrotuberous ligament, periostium of the pubic bone (not shown in FIG. 6), pubourethral ligament (also not shown, but connects urethra to pubic bone), arcus tendineus (not shown), anococcygeal body ligament (not specifically shown), sacrospinous ligament (not shown in FIG. 6), a region of the ischial spine, or ischial tuberosity. Alternately or additionally, the tissue support portion or an extension portion can be attached to periostium of the pubic bone in a region of the ischial tuberosity. Alternately or additionally, a tissue support portion or extension portion can be extended through a tissue path between levator ani muscle and obturator internus muscle and attached at the arcus tendineus (white line), at the obturator membrane, or extend through the obturator foramen to an external incision at the inner thigh.

In general for a fecal incontinence sling and other pelvic floor and levator ani muscle repairs, anchoring points for a tissue fastener such as a self-fixating tip or a bone anchor could include sacrotuberous ligament laterally or the periostium of the pubic bone—specifically by the ischial tuberosity. Additionally, a bone anchor could be placed at the ischial tuberosity to attach the sling internally at the pelvic region. The sling can pass under the external anal sphincter and be attached laterally at each side (e.g., at the ischial tuberosity). According to one specific embodiment, the sling could be placed using self-fixating tips. In addition, the sling and self-fixating tips could be placed between the levator ani muscle and the obturator internus muscle, attaching the fascial white line or "arcus tendineus." Optionally and preferably the sling could be placed directly over the superficial transverse perineal muscle, adding the foundational support of the pelvic floor.

In this embodiment, while wishing to not be bound by theory, it is believed that the sling will not only function to restore the anal rectal angle but will also or alternately provide a backstop for the levator muscles. This will allow the anus more support for closure and maintenance of continence. Restoring the anchoring point of the levator ani muscles allows them to contract more efficiently to close off the anal canal.

Alternately or in addition, the sling can be attached to the puborurethral ligament, which may restore the rectal angle. Curing fecal incontinence in this manner is at least in part due to restoring the leverage points for the levator plate and longitudinal muscle of the anus, in addition to any improvement due to restoring the anal rectal angle.

Yet another possible placement for a tissue fastener can be the sacrum, e.g., using a bone anchor, or at the sacrospinous ligament or anococcygeal body ligament, by attaching a tissue fastener. The various meshes described herein can also be anchored in the anorectal hiatus so as to recreate the puborectalis and pubococcygeal muscle. Other anchor points include: periostium, fibrous tissue, or underside of the muscle.

The implant can also be made with a combination of synthetic and biologic material (such as porcine dermis) or can be made entirely of the biologic material and can also include a coating to enhance ingrowth and adoption by the body. In another embodiment, the implants can include stem cells that will help to regenerate the muscle tissue and build a thicker and stronger muscle. The central portion of the levator muscle can also be injected with stem cells at the same time the implant is being placed in the patient.

All of the described embodiments and surgical methods are applicable to both women and men. In addition, the implants can be populated with one or more electrodes for electrical stimulation of the levator ani muscles or any of the nearby pelvic muscles to assist in the treatment of the patient. Electrodes and implantable pulse generators applicable to this embodiments and that can be incorporated into the disclosed implants can be found in US Publication No. 2005/0049648 and WO 2007/106303A2, which are herein incorporated by reference in its entirety.

According to still further embodiments, an extension portion of an implant can pass through a tissue path in the pelvic region to an external incision, such as: through a tissue path that extends to an external incision in at the abdomen; through a tissue path that extends above the pubic bone to a suprapubic incision; through a tissue path that extends through an obturator foramen and to an external incision at the inner thigh; through a tissue path that extends laterally through a region of the coccyx to an external incision adjacent to the coccyx; or through a tissue path that extends to an external incision at a perarectal or perianal region.

As is apparent from the present description, an implant can be installed by any one or combination of incisions that can result in direct access to levator or coccygeus tissue, or access to a tissue path that extends from the external incision to levator or coccygeus tissue. Examples are a perarectal incision that allows open access to tissue of the pelvic floor; a small external perarectal incision that can allow a tissue path to extend from the external perirectal incision to tissue of the pelvic floor; a small external incision in a region of the coccyx that can allow a tissue path to extend from the external incision to tissue of the pelvic floor; a suprapubic incision that involves a small or large external incision at the suprapubic position; a transobturator approach whereby an extension portion of an implant can be placed through a tissue path leading from an external incision at the inner thigh, through an obturator, and to an implant located to support tissue of the pelvic floor; the use of a Kraske incision, e.g., an incision under the rectum; a "modified Kraske" incision; a perineal incision; and a vaginal incision. Certain useful methods can involve reduced need for external incisions based on the use of internal tissue fasteners such as self-fixating tips, to fasten the implant to internal tissue of the pelvic region and eliminate the need for exit points of extension portions.

According to one exemplary tissue path, the transobturator tissue path, extension portion of an implant can extend from a tissue support portion at the levator tissue, through a superior aspect of the obturator foreman. Passage through the superior aspect—very top of the obturator foramen—may result in support such as would be provided by the pubococcygeal ligament, and tightening of the levator hiatus, which can repair the perineal body and restore the anorectal angle. Generally, transobturator tissue approaches are described at pending application Ser. No. 11/347,047 "Transobturator Methods for Installing Sling to Treat Incontinence, and Related Devices," filed Feb. 3, 2006, and at US publication 2005/0143618 (Ser. No. 11/064,875) filed Feb. 24, 2005, the entireties of these being incorporated herein by reference.

Figure 7:
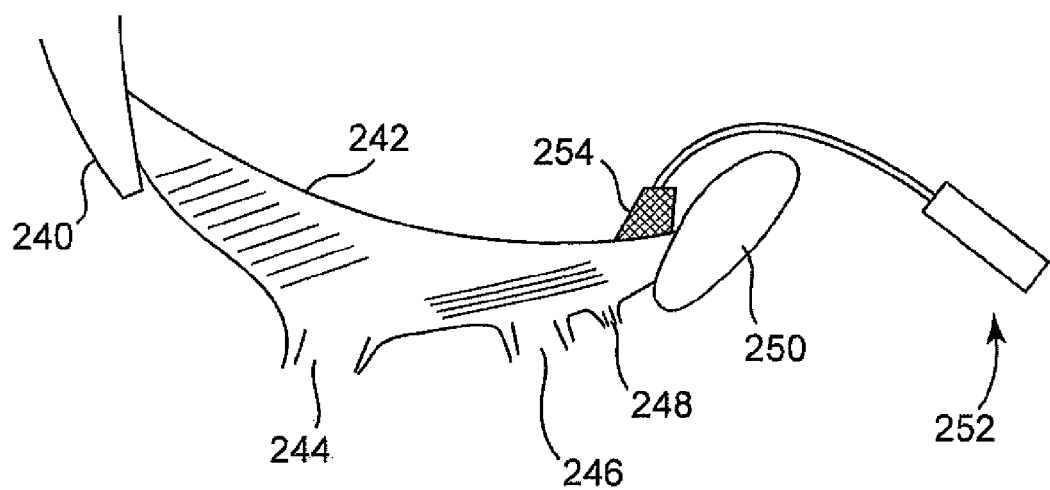
FIG. 7 illustrates an embodiment of tissue path as described.

An example of a suprapubic approach (external incision approach) is illustrated at FIG. 7. Referring to FIG. 7, relevant anatomy includes coccyx 240, white line 242, rectum 244, vagina 246, urethra 248, and pubic bone 250. Insertion tool 252 includes a needle connected to implant 254. A portion (not shown) of implant 254 is located to contact levator tissue and support levator tissue, and a portion (illustrated) such as an extension portion, optionally including a connector for engaging the end of the needle, connects to the needle and is pulled through a tissue path leading from the levator to an external incision in the suprapubic region.

In general, an incision that is in a region of the perineum can be an incision at that location, e.g., between a vagina and an anus in a female. An incision in the perirectal region can be, for example, within 1 to 4 centimeters of the anus.

Figure 8:
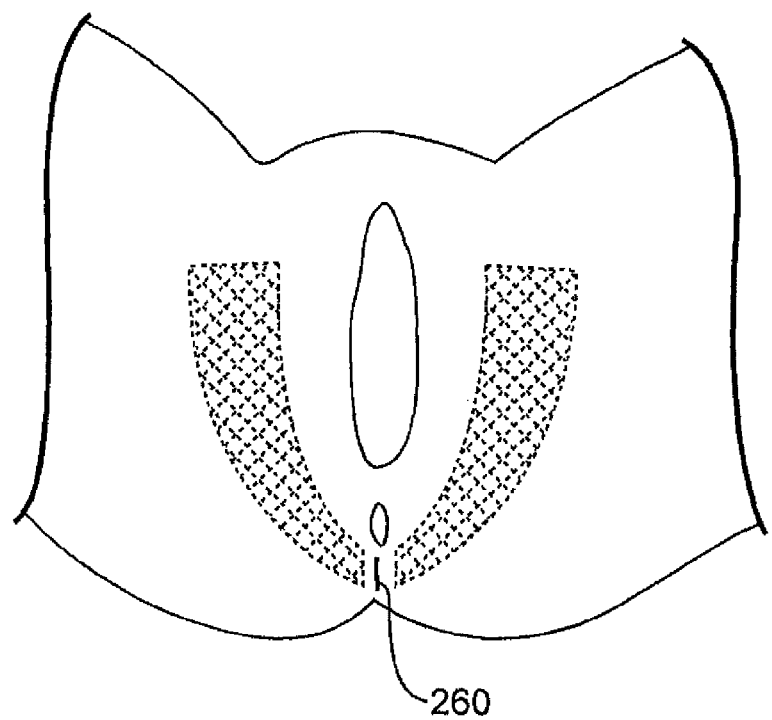
FIGS. 8, 8A, 8B, and 8C, illustrate embodiments of incisions as described.
Figure 8A:
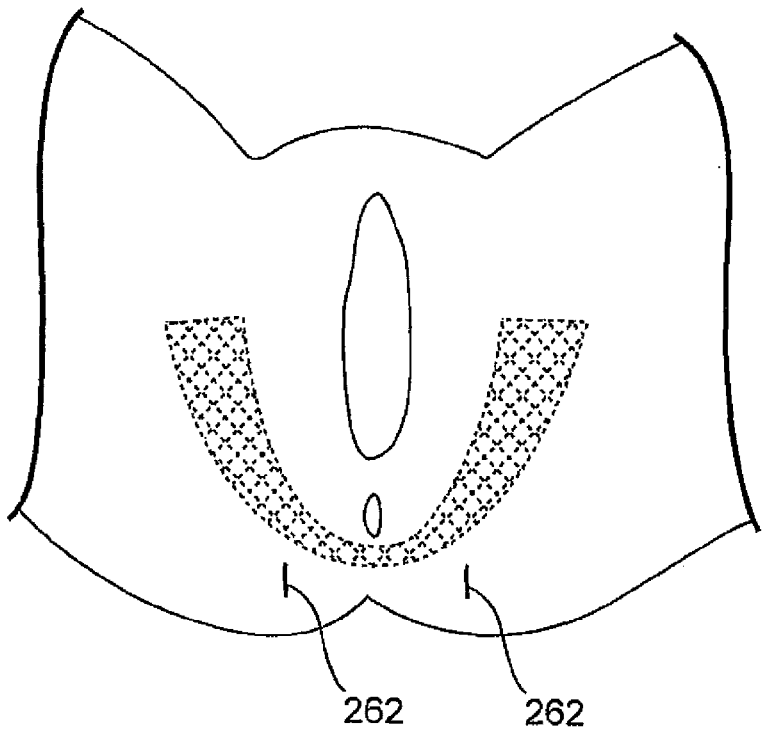
Figure 8B:
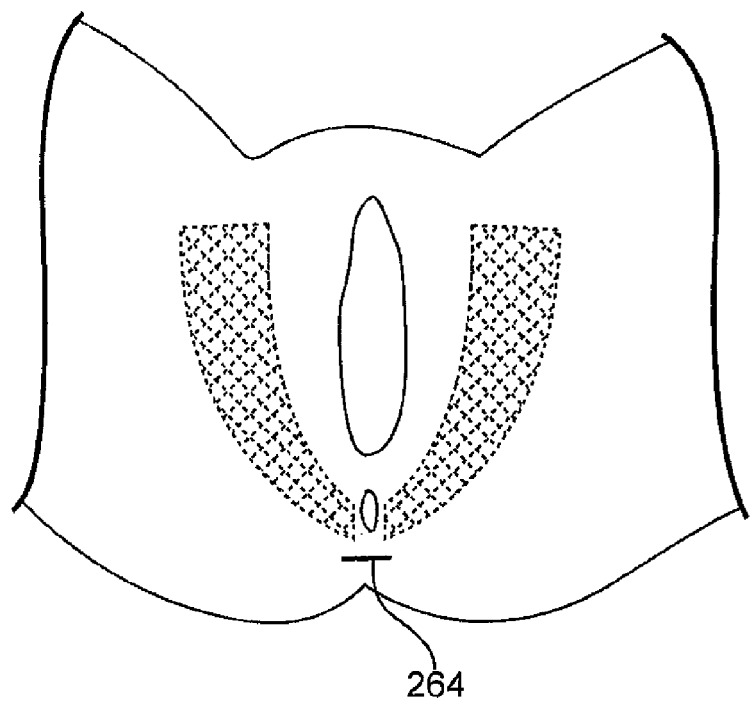
Figure 8C:
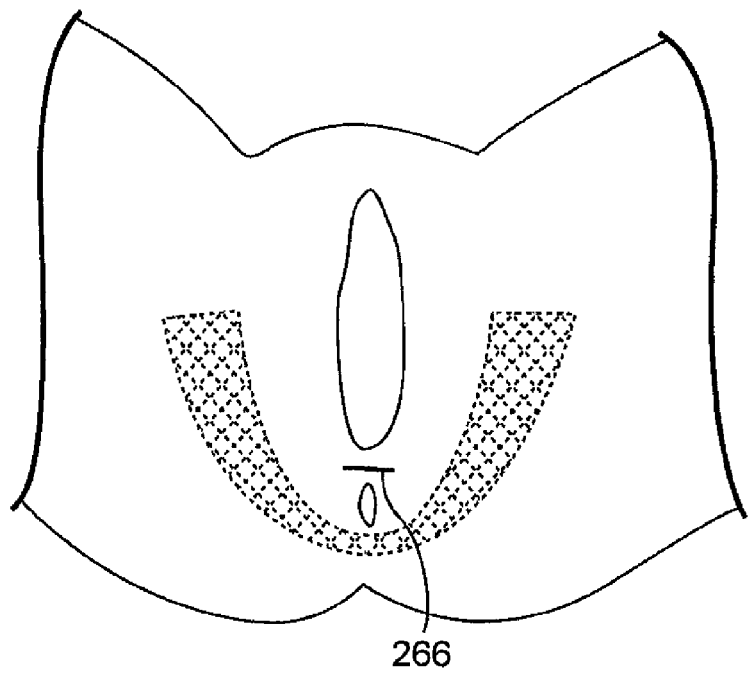

An example of a "modified" Kraske incision (260) (modified to a vertical orientation) is illustrated at FIG. 8. An example of a perirectal or perianal incision (262) is illustrated at FIG. 8A. Another example of a perirectal or perianal incision (264) is illustrated at FIG. 8B. An example of a perineal incision (266) is illustrated at FIG. 8C. All of these types of incision allow access to pelvic floor tissue for implantation of one or two portions of a sling in contact with levator tissue (illustrated in shadow).

Figure 9B:
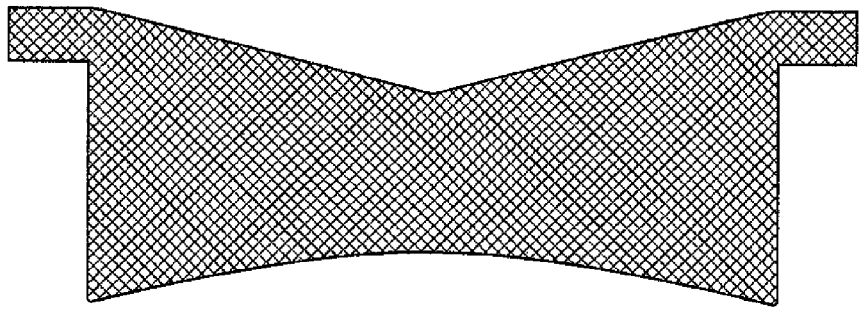
FIGS. 9A and 9B illustrate other embodiments of the mesh implant that include one or two arms for implantation and a variation in the central portion of the implant.
Figure 9A:
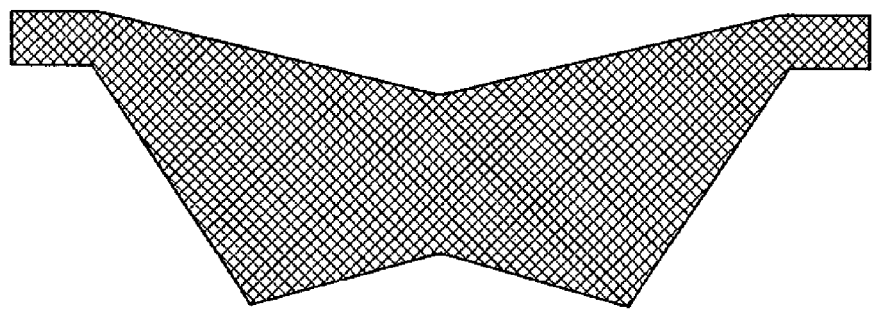

Referring now FIGS. 9A and 9B, there are shown other embodiments of the mesh implant that include one or two arms for implantation and a variation in the central portion of the implant. The implant can be modified to include one or more anchors or anchoring devices at each of the various points that protrude from the mesh or substitute one or more anchors with mesh arms to enhance anchoring in the pelvic tissue (see upper arms) and to assist in repositioning or tensioning of the mesh implant. The arms can also be used to correct avulsions in the one or more of the levator ani muscles as the mesh arms are pulled up to or through the obturator foramen. In a related embodiment, the anchor points below the mesh arms can be anchored in the ishcial spine, illiococcygeous muscle, sacrospinous ligament or the sacrotuberous ligament. The center portion of the mesh implant supports the rectum, the puborectalis muscle and/or the perineum. Ischial spine fixation can be achieved through mesh arms introduced transvaginally or through soft tissue fixation (anchors, etc.).

The obturator passes can also be made with anchor/fixation elements in the obturator membrane, cooper's ligament, puborectalis muscle, or the whiteline. Mesh arms can also pass through these various structures. The various passes can be used to tension against the rectum/puborectalis muscles to correct defecatory disorders and fecal incontinence. They can also be used to repair levator avlusion/puborectalis avulsion.

Figures 10A, 10B:
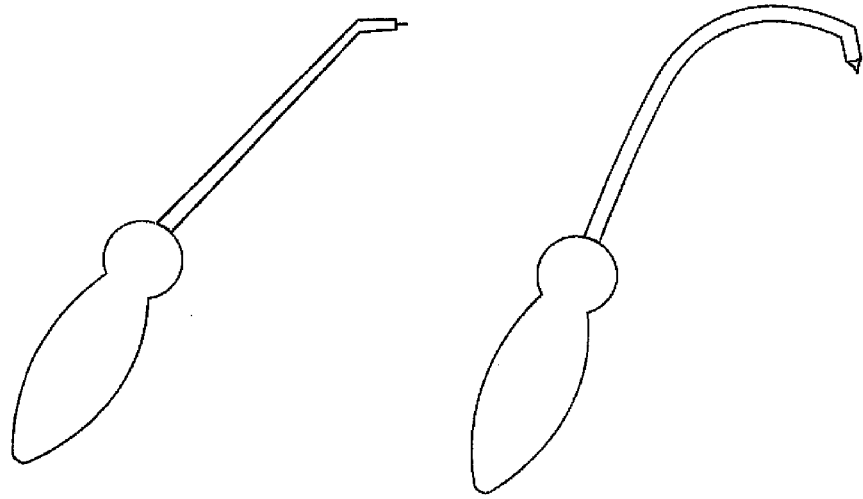
FIGS. 10A and 10B illustrate implantation needles for implanting the mesh implants of the embodiments described herein.

FIGS. 10A and 10B illustrate implantation needles for implanting the mesh implants of the embodiments described herein, which have self limiting depth features to ensure the tissues are not pierced too deeply. Also straight, helical and curved needles, as described in U.S. Publication no. 2005/0250977; 2005/0245787 and 2004/0039453, which are herein incorporated by reference in their entirety, can also be used with their associated tunneling paths and techniques. In a related embodiment, a depth limiting feature such as a sheath design or a mechanical stop or a bend in the needle to facilitate correct depth placement. Also inside out as opposed to the outside in implantation approach is a possible variation to the described embodiments (similar to the ISCP methods and techniques). The needle can exit the body through skin incisions or simply push the anchoring device up to a point in the obturator or the ischial spine with connection to the implant being made via palpation. The mesh arm can be drawn in from the outside and then cut off within the vaginal dissection. In the various embodiments disclosed, the mesh implant is about 14-18 cm in length and about 6-10 cm in width from the end of the mesh to the first end of the mesh arm (see FIG. 9B) the center portion of the mesh implants are about 2-3 cm. In FIG. 9B, the side portions angling from the arms to the end of the center portion are about 6-10 cm. The average stiffness of the mesh for well is about 3.63 with a min of 3.18 and a max of 4.59 and the standard deviation being about 0.46 when various measurements were done. As for warp, the average was 3.03, the min was 2.65, max was 4.23 and the standard deviation was about 0.46.

Figures 10C, 10D, 10E:
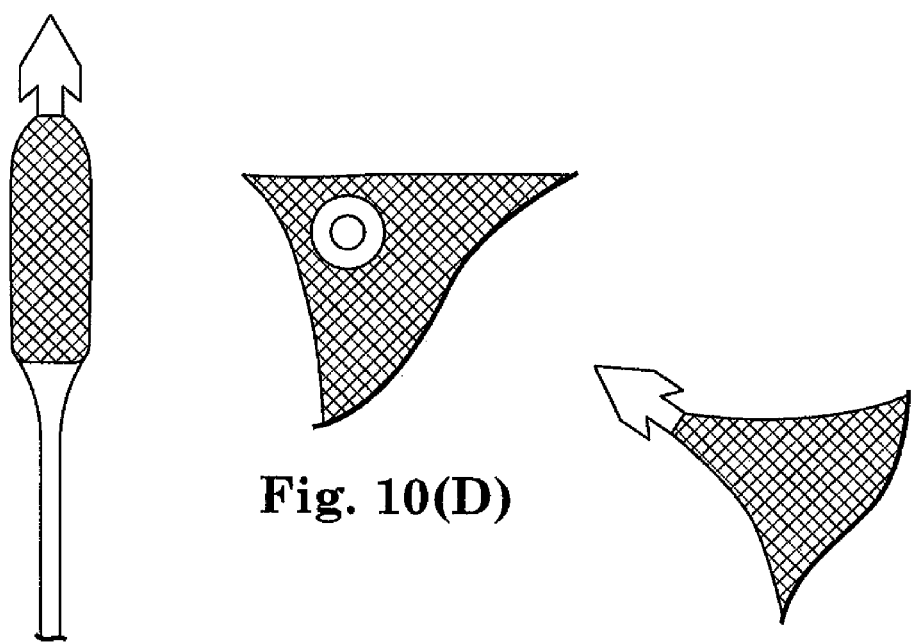
FIGS. 10C-E illustrate a modification to the embodiments of the implants to include grommets instead of anchors.

FIGS. 10C-E illustrate a various to the embodiments of the implants wherein grommets can also be included in the corners of the implants to pass through other fixation means with anchoring elements or sutures or sutures with anchors at the ends so as to tie the anchored sutures to the mesh via the grommets. With these embodiments, the arm/anchor fixation the implants can span the levators, restore ballooned levators or correct an avulsion along the sidewall and/or whiteline.

In various related embodiments, the implant can replace the entire sacraltuberous ligament as opposed to just attaching to it. Any non-continuos sling would be also be applicable such that it does not go on the posterior side of the anus. For example, it could attach to the lateral sides of the external sphincter and extend towards the obturator or any other suspensory structure and may not need to be under the anus. This would allow the anus to expand unrestricted and may give the levator plate the support it needs to be leveraged. In addition, an implant that is positioned anterior to the anus would be applicable. In a related embodiment, the implant would replace the perianal muscle or attaches to the superior portion of the external sphincter. Variable weave meshes with varying elasticities such as a mesh that is highly elastic around the anus to allow stool to pass would be incorporated into any of the described embodiments. Porcine dermis or meshes with growth factors can also be incorporated into the implants. Curved and helical needles, such as described in U.S. Pat. No. 6,911,003 can also be used to implant these implants. Superior aspect of the obturator foreman as a passage point for at least one needle or would be an attachment point for the mesh so as to accomplish internal anchoring. In another embodiment, the implant can go through the superior aspect—very top—so as to recreate the pubococcegeal ligament and tightening of the levator hiatus which would repair the perianal body and restore the anorectal angle. Tensioning sutures—adjustment sutures can also be included in any of the implants. Even sutures that come out the gluteus that can be used to tightened or relocate the implant later. The sacrum can also be used as attachment points. The implants can have multiple legs, 2, 4, 6 or other combination with odd number of legs. In another embodiment, the implant is tunneled under the anus to form a continuous circle then optionally continuing the legs superficially under the anus. Finally, a bulking agent can be used to fill the ishiorectal fossa and push the levators inwards.

Examples of various tissue paths, relevant anatomy, implant materials, features of implants (e.g., connectors, tensioning devices), insertion tools, are described, for example, in U.S. Publication Nos. 2002/0161382, (Ser. No. 10/106,086) filed Mar. 25, 2002; 2005/0250977 (Ser. No. 10/840,646) filed May 7, 2004; and 2005/0245787 (Ser. No. 10/834,943) filed Apr. 30, 2004; 2005/0143618 (Ser. No. 11/064,875) filed Feb. 24, 2005; and U.S. Pat. No. 6,971,986 (Ser. No. 10/280,341) filed Oct. 25, 2002; U.S. Pat. No. 6,802,807 (Ser. No. 09/917,445) filed Jul. 27, 2001; U.S. Pat. No. 6,612,977 (Ser. No. 09/917,443) filed Jul. 27, 2001; U.S. Pat. No. 6,911,003 (Ser. No. 10/377,101) filed Mar. 3, 2003; U.S. Pat. No. 7,070,556 (Ser. No. 10/306,179) filed Nov. 27, 2002, PCT/US2007/004015 "Surgical Articles and Methods for Treating Pelvic Conditions," filed Feb. 16, 2007; PCT/US2007/014120 "Surgical Implants, Tools, and Methods for Treating Pelvic Conditions, filed Jun. 15, 2007; the entireties of each of these being incorporated herein by reference.

EXAMPLE

Levator Distention Repair

1. Blunt Dissection
  a. Make a transverse incision, approximately 2 cm inferior to the anus and 3 cm long, similar to a Krasky incision,
    i. There is an option here of dissecting through or superficial to the anococcygeal ligament. Dissection superficial to the ligament may provide a backstop for the rectum without putting it in tension or risking erosion. However, for severe fecal incontinence, or if greater tensioning was required, the ligament could be dissected as well and the mesh placed behind it.
  b. Insert a finger into the incision and tunnel toward the ischial spine on the patient left side. Use blunt dissection with your finger to open the space to the spine. The finger will lie between the levator muscle (medial) and fatty tissue (lateral).
  c. Make a sweeping motion with your finger, creating a space between the fat and muscle, between the ischial spine and the posterior edge of the obturator foramen on the inferior pubic ramus.
  d. Repeat B & C on the patient right side.
2. Mesh Placement with Needle
  a. Insert a needle through the anchor on one of the mesh arms.
  b. Placing your finger on the inferior pubic ramus near the obturator foramen, run the needle along your finger until the end with the anchor pushes into the tissue, into the obturator internus muscle.
  c. Remove the needle by pulling out of the incision. Give the mesh a tug to ensure the anchor has caught tissue. Insert the needle into the anchor on the other mesh arm.
  d. Place your finger on the ischial spine, and run the needle along your finger until the end with the anchor pushes into the tissue, near the ischial spine in the levator muscle.
  e. Remove the needle.
  f. Sweep along the mesh, smoothing the area between the anchors and sweeping the tail end beneath the rectum.
  g. Repeat steps A—F on the contralateral side.
3. Close Incision with Suture.
  a. If the ligament was dissected, rejoin the ends of the ligament over the mesh before closing the incision.

The invention claimed is:

1. A pelvic implant for supporting levator tissue, the implant comprising a tissue support portion bounded by:
   an anterior side extendable from an anterior region of the pelvic region to a region of medial levator tissue, the anterior region selected from a region of the obturator foramen, a region of the arcus tendineus, and a region of puborectalis muscle,
   a posterior side extendable from a posterior region of the pelvic region to a region of medial levator tissue, the posterior region selected from a region of the ischial spine, an ischial tuberosity, a sacrospinous ligament, a sacrotuberous ligament, and a sacrum,
   a grommet at a corner of the implant,
   at least one lateral end extendable from the anterior region to the posterior region, and
   fixation means comprising an anchoring element and mesh, the fixation means being passable through the grommet when the tissue support portion is located at a region of levator tissue,
wherein the tissue support portion comprises first and second opposing shaped portions, each shaped portion comprising:
   a portion of the anterior side of the tissue support portion;
   a portion of the posterior side of the tissue support portion, and
   the at least one lateral end of the tissue support portion:
and wherein
   the first and second shaped portions are connected at a medial portion,
   the implant has a length in the range from 14 to 18 centimeters,
   the medial portion has a dimension in the range from about 2 to 3 centimeters, and
   the at least one lateral end has a length in the range from about 6 to 10 centimeters.

2. The implant of claim 1 wherein the shaped portions have a shape substantially of a figure selected from a square, a rhombus, a symmetric trapezoid, a non-symmetric trapezoid, a symmetric rectangle, and a non-symmetric rectangle.

3. The implant of claim 1 comprising one or two extension portions located at corners of the shaped portions along the at least one lateral end.

4. A kit comprising an implant according to claim 1, the anchoring element comprising a self-fixating tip, and the kit further comprising an insertion tool that engages the self-fixating tip.

5. A kit according to claim 4 wherein the insertion tool comprises an elongate needle having a shape selected from the group consisting of: a straight form, a curve in two dimensions, a curve in three dimensions, and a helical curve.

6. A pelvic implant for supporting levator tissue, the implant comprising two opposing tissue support portions, each opposing tissue support portion comprising:
   an anterior side extendable from an anterior region of the pelvic region to a region of medial levator tissue, the anterior region selected from a region of the obturator foramen, a region of the arcus tendineus, and a region of puborectalis muscle,
   a posterior side extendable from a posterior region of the pelvic region to a region of medial levator tissue, the posterior region selected from a region of the ischial spine, an ischial tuberosity, a sacrospinous ligament, a sacrotuberous ligament, and a sacrum,
   a grommet, and
   a lateral end extendable from the anterior region to the posterior region when the two tissue support portions are located at a region of levator tissue, and wherein:
   the two opposing tissue support portions are connected at a medial portion,
   the implant has a length in the range from 14 to 18 centimeters,
   the medial portion has a dimension in the range from about 2 to 3 centimeters, and
   the lateral end has a length in the range from about 6 to 10 centimeters.

7. An implant according to claim 6 wherein the grommet is at a corner of the implant.

8. An implant according to claim 7 further comprising fixation means with an anchoring element, the fixation means being capable of passing through the grommet.

9. A kit comprising a pelvic implant for supporting levator tissue, the implant comprising two opposing tissue support portions, each opposing tissue support
   portion comprising:
      an anterior side extendable from an anterior region of the pelvic region to a region of medial levator tissue, the anterior region selected from a region of the obturator foramen, a region of the arcus tendineus, and a region of puborectalis muscle,
      a posterior side extendable from a posterior region of the pelvic region to a region of medial levator tissue, the posterior region selected from a region of the ischial spine, an ischial tuberosity, a sacrospinous ligament, a sacrotuberous ligament, and a sacrum,
      a grommet at a corner of each of the two tissue support portions,
      a lateral end extendable from the anterior region to the posterior region, and
      a self-fixating tip,
   wherein:
      the two opposing tissue support portions are connected at a medial portion,
      the implant has a length in the range from 14 to 18 centimeters,
      the medial portion has a dimension in the range from about 2 to 3 centimeters, and
      the lateral end has a length in the range from about 6 to 10 centimeters;
   the kit comprising an insertion tool that engages the self-fixating tip.

10. A kit according to claim 9 comprising fixation means capable of passing through the grommet, the fixation means comprising mesh and a self-fixating tip.

* * * * *

UNITED STATES PATENT AND TRADEMARK OFFICE
CERTIFICATE OF CORRECTION

| | |
|---|---|
| PATENT NO. | : 8,517,914 B2 |
| APPLICATION NO. | : 12/447073 |
| DATED | : August 27, 2013 |
| INVENTOR(S) | : Anderson et al. |

Page 1 of 2

It is certified that error appears in the above-identified patent and that said Letters Patent is hereby corrected as shown below:

On the Title Page:
    Page 2, in item (56), under "OTHER PUBLICATIONS", in Column 1, Line 5, delete "Dunction" and insert -- Voiding Dysfunction --, therefor; Page 2, in item (56), under "OTHER PUBLICATIONS", in Column 1, Line 6, delete "(2001) Voidingysf." and insert -- (2001). --, therefor; Page 2, in item (56), under "OTHER PUBLICATIONS", in Column 2, Line 27, delete "et al," and insert -- et al., --, therefor.

Page 3, in item (56), under "OTHER PUBLICATIONS", in Column 1, Line 6, delete "168(4):318-22," and insert -- 168(4):318-322, --, therefor; Page 3, in item (56), under "OTHER PUBLICATIONS", in Column 1, Line 8, delete "Uro ." and insert -- Urol. --, therefor; Page 3, in item (56), under "OTHER PUBLICATIONS", in Column 1, Line 8, delete "12(4):353-58," and insert -- 12(4):353-358, --, therefor; Page 3, in item (56), under "OTHER PUBLICATIONS", in Column 1, Lines 10-11, delete "Sergical Safety, Obstet. Gynecol. 97:873-79," and insert -- Surgical Safety, Obstet. Gynecol. 97:873-879, --, therefor; Page 3, in item (56), under "OTHER PUBLICATIONS", in Column 2, Line 4, delete "182-86." and insert -- 182-186. --, therefor; Page 3, in item (56), under "OTHER PUBLICATIONS", in Column 2, Lines 5-6, delete "procedure,:" and insert -- procedure, --, therefor.

In the Specification:
    Column 1, Line 66, delete "iliococcygeous" and insert -- iliococcygeus --, therefor.
    Column 6, Line 23, delete "tranvaginally.)" and insert -- transvaginally.) --, therefor.
    Column 11, Line 26, delete "iliococcygeous" and insert -- iliococcygeus --, therefor; Column 11, Line 61, delete "implant 12" and insert -- implant 2 --, therefor.
    Column 12, Line 31, delete "iliococcygeous" and insert -- iliococcygeus --, therefor.
    Column 14, Line 18, delete "coccygeous muscle, iliococcygeous" and insert -- coccygeus muscle, iliococcygeus --, therefor; Column 14, Line 29, delete "coccygeous, iliococcygeous)," and insert -- coccygeus, iliococcygeus), --, therefor.
    Column 15, Line 58, delete "an view" and insert -- a view --, therefor.

Signed and Sealed this
Seventeenth Day of February, 2015

Michelle K. Lee
*Deputy Director of the United States Patent and Trademark Office*

CERTIFICATE OF CORRECTION (continued)

Column 17, Line 7, delete "puborurethral" and insert -- pubourethral --, therefor; Column 17, Lines 33-34, delete "this embodiments" and insert -- this embodiment --, therefor; Column 17, Line 48, delete "perarectal" and insert -- perirectal --, therefor; Column 17, Line 53, delete "perarectal" and insert -- perirectal --, therefor; Column 17, Line 55, delete "perarectal" and insert -- perirectal --, therefor.

Column 18, Lines 55-56, delete "ishcial spine, illiococcygeous" and insert -- ischial spine, iliococcygeus --, therefor; Column 18, Line 67, delete "avlusion/puborectalis" and insert -- avulsion/puborectalis --, therefor.

Column 19, Line 37, delete "sacraltuberous" and insert -- sacrotuberous --, therefor; Column 19, Line 38, delete "non-continuos sling would be also be" and insert -- non-continuous sling would also be --, therefor; Column 19, Line 58, delete "pubococcegeal" and insert -- pubococcygeal --, therefor.

Column 20, Line 2, delete "ishiorectal" and insert -- ischiorectal --, therefor; Column 20, Line 29, delete "Krasky" and insert -- Kraske --, therefor.

In the Claims:
Column 21, Line 26, in Claim 1, delete "portion:" and insert -- portion; --, therefor.
Column 22, Line 27, in Claim 9, delete "portion comprising:" and insert the same at Line 26, after "support", as a continuation sub-point.

UNITED STATES PATENT AND TRADEMARK OFFICE
CERTIFICATE OF CORRECTION

PATENT NO.        : 8,517,914 B2                                                              Page 1 of 1
APPLICATION NO.   : 12/447073
DATED             : August 27, 2013
INVENTOR(S)       : Anderson et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1049 days.

Signed and Sealed this
Fifteenth Day of September, 2015

Michelle K. Lee
*Director of the United States Patent and Trademark Office*